US012349957B2

(12) United States Patent
Lederman et al.

(10) Patent No.: US 12,349,957 B2
(45) Date of Patent: Jul. 8, 2025

(54) INNER CURVATURE CHARGE CONCENTRATION DEVICE FOR TISSUE LACERATION

(71) Applicant: The United States of America, as represented by the Secretary, Department of Health and Human Services, Bethesda, MD (US)

(72) Inventors: Robert J. Lederman, Chevy Chase, MD (US); Jaffar M. Khan, Washington, DC (US); Toby Rogers, Washington, DC (US)

(73) Assignee: The USA, as represented by the Secretary, Dept. of Health and Human Services, Bethesda, MD (US)

( * ) Notice: Subject to any disclaimer, the term of this patent is extended or adjusted under 35 U.S.C. 154(b) by 463 days.

(21) Appl. No.: 16/954,710

(22) PCT Filed: Feb. 19, 2019

(86) PCT No.: PCT/US2019/018503
§ 371 (c)(1),
(2) Date: Jun. 17, 2020

(87) PCT Pub. No.: WO2019/164806
PCT Pub. Date: Aug. 29, 2019

(65) Prior Publication Data
US 2020/0383717 A1 Dec. 10, 2020

Related U.S. Application Data

(60) Provisional application No. 62/633,791, filed on Feb. 22, 2018.

(51) Int. Cl.
*A61B 18/14* (2006.01)
*A61B 18/08* (2006.01)
(Continued)

(52) U.S. Cl.
CPC ........ *A61B 18/082* (2013.01); *A61B 18/1206* (2013.01); *A61B 18/149* (2013.01);
(Continued)

(58) Field of Classification Search
CPC .............. A61B 18/082; A61B 18/1206; A61B 2018/00369; A61B 2018/00601;
(Continued)

(56) References Cited

U.S. PATENT DOCUMENTS 5,318,564 A * 6/1994 Eggers .................. A61B 18/14
606/49
5,836,947 A * 11/1998 Fleischman ............ A61N 1/056
606/41

(Continued)

FOREIGN PATENT DOCUMENTS

CN 101309654 11/2008
CN 203195801 9/2013
(Continued)

OTHER PUBLICATIONS

Khan Jaffar M et al., "Intentional Laceration of the Anterior Mitral Valve Leaflet to Prevent Left Ventricular Outlfow Tract Obstruction During Transcatheter Mitral Valve Replacement Pre-Clinical Findings", Sep. 5, 2016, Elsevier, vol. 9, No. 17, p. 1835-1843 (Year: 2016).*

(Continued)

*Primary Examiner* — Sean W Collins
(74) *Attorney, Agent, or Firm* — Sheridan Ross P.C.

(57) ABSTRACT

Disclosed monopolar and bipolar tissue lacerators can comprise a wire partially covered by electrical insulation, wherein the wire has a kink defining an inner curvature, wherein the wire is exposed through the insulation at one or two exposed regions along or near the inner curvature of the kink, wherein the wire is configured to conduct electrical (Continued)

energy through the one or two exposed regions and through a tissue target positioned adjacent the inner curvature to lacerate the tissue target via the electrical energy. The tissue target can be a native or prosthetic heart valve leaflet in a patient's heart.

12 Claims, 18 Drawing Sheets

(51) Int. Cl.
    *A61B 18/12*     (2006.01)
    *A61B 18/00*     (2006.01)
(52) U.S. Cl.
    CPC ............... *A61B 18/1492* (2013.01); *A61B 2018/00083* (2013.01); *A61B 2018/00369* (2013.01); *A61B 2018/00601* (2013.01); *A61B 2018/1253* (2013.01); *A61B 2018/126* (2013.01); *A61B 2018/141* (2013.01); *A61B 2018/144* (2013.01); *A61B 2218/002* (2013.01)
(58) Field of Classification Search
    CPC ...... A61B 2018/1253; A61B 2018/126; A61B 2218/002; A61B 2018/00083; A61B 2018/1407; A61B 2018/144; A61B 18/149; A61B 18/1492; A61B 2018/1425; A61B 2018/142; A61F 2/2412
    See application file for complete search history.

(56) References Cited

U.S. PATENT DOCUMENTS

| | | | | |
|---|---|---|---|---|
| 6,050,995 | A * | 4/2000 | Durgin | A61B 18/14 606/50 |
| 6,582,425 | B2 | 6/2003 | Simpson | |
| 6,773,432 | B1 * | 8/2004 | Clayman | A61B 18/14 606/49 |
| 2004/0059351 | A1 | 3/2004 | Eigler et al. | |
| 2005/0171532 | A1 * | 8/2005 | Ciarrocca | A61B 18/14 606/50 |
| 2009/0192510 | A1 * | 7/2009 | Bahney | A61B 18/1482 606/45 |
| 2009/0281541 | A1 * | 11/2009 | Ibrahim | A61B 18/1492 606/42 |
| 2014/0163550 | A1 * | 6/2014 | Besser | A61B 18/1492 606/41 |
| 2015/0066016 | A1 * | 3/2015 | Miles | A61B 18/1492 606/34 |
| 2015/0320481 | A1 * | 11/2015 | Cosman, Jr. | A61B 34/10 606/35 |
| 2016/0175042 | A1 * | 6/2016 | McLawhorn | A61B 18/14 606/41 |
| 2017/0245909 | A1 * | 8/2017 | Konesky | A61B 18/042 |
| 2017/0258521 | A1 * | 9/2017 | Asirvatham | A61B 17/00234 |

FOREIGN PATENT DOCUMENTS

| | | | |
|---|---|---|---|
| CN | 107205816 | 9/2017 | |
| WO | WO-2015155794 A2 * | 10/2015 | ......... A61B 18/1492 |

OTHER PUBLICATIONS

Babaliaros et al., "Intentional Percutaneous Laceration of the Anterior Mitral leaflet to Prevent Outflow Obstruction During Transcatheter Mitral Valve Replacement: First-in-Human Experience," *Journal of the American College of Cardiology Interventions*, 10(8):798-809 (Apr. 24, 2017).
International Search Report and Written Opinion for related International Application No. PCT/US2019/018503, 10 pages, mailed May 29, 2019.
Khan et al., "Intentional Laceration of the Anterior Mitral valve leaflet to Prevent Left Ventricular Outflow Tract Obstruction During Transcatheter Mitral Valve Replacement: Pre-Clinical Findings," *Journal of the American College of Cardiology Interventions*, 9(17):1835-1843 (Sep. 12, 2016).
Khan et al., "LAMPOON to Facilitate Tendyne Transcatheter Mitral Valve Replacement," *Journal of the American College of Cardiology Cardiovascular Interventions*, 11(19):2014-2017 (Oct. 8, 2018).
Khan et al., "LAMPOON to Prevent LVOT Obstruction During Transcatheter Mitral Valve Replacement (TMVR): Prospective Multicenter Trial Results," Presentation OPCI 2019, 21 pages (Mar. 8, 2019).
Khan et al., "Transcatheter Laceration of Aortic Leaflets to Prevent Coronary Obstruction During Transcatheter Aortic Valve Replacement: Concept to First-in-Human," *Journal of the American College of Cardiology Cardiovascular Interventions*, 11(7):677-689 (Apr. 9, 2018).
Case "Tip-to-Base LAMPOON to Prevent Left Ventricular Outflow Tract Obstruction in Valve-in-Valve Transcatheter Mitral Valve Replacement," JACC: Cardiovascular Interventions, May 2020, vol. 13, No. 9, pp. 1126-1128.
Greenbaum et al. "First-in-human transcatheter pledget-assisted suture tricuspid annuloplasty for severe tricuspid insufficiency," Catheterization & Cardiovascular Invterventions, May 2020, 5 pages.
Kamioka et al. "Bi-Silica During Transcatheter Aortic Valve Replacement for Noncalcific Aortic Insufficiency: Initial Human Experience," JACC: Cardiovascular Interventions, Nov. 2018, vol. 11, No. 21, pp. 2237-2239.
Kasel et al. "International LAMPOON: first European experience with laceration of the anterior mitral valve leaflet prior to transseptal transcatheter mitral valve implantation," EuroIntervention, Sep. 2018, vol. 14, No. 7, pp. 746-749.
Khan et al. "The Basilica Trial: Prospective Multicenter Investigation of Intentional Leaflet Laceration to Prevent TAVR Coronary Obstruction," JACC: Cardiovascular Interventions, 2019, vol. 12, No. 13, pp. 1240-1252.
Khan et al. "Transcatheter Mitral Valve Replacement After Transcatheter Electrosurgical Laceration of Alfieri STItCh (ELASTIC): First-in-Human Report," JACC: Cardiovascular Interventions, Apr. 2018, vol. 11, No. 8, pp. 808-811.
Khan et al. "Predicting Left Ventricular Outflow Tract Obstruction Despite Anterior Mitral Leaflet Resection: The "Skirt NeoLVOT"," JACC: Cardiovascular Imaging, Sep. 2018, vol. 11, No. 9, pp. 1356-1359.
Khan et al. "Transcatheter Electrosurgery: JACC State-of-the-Art Review," Journal of the American College of Cardiology, Mar. 2020, vol. 75, No. 12, pp. 1455-1470.
Khan et al. "Anterior Leaflet Laceration to Prevent Ventricular Outflow Tract Obstruction During Transcatheter Mitral Valve Replacement," Journal of the American College of Cardiology, May 2019, vol. 73, No. 20, pp. 2521-2534.
Khan et al. ""Rescue" LAMPOON to Treat Transcatheter Mitral Valve Replacement-Associated Left Ventricular Outflow Tract Obstruction," JACC: Cardiovascular Interventions, Jul. 2019, vol. 12, No. 13, pp. 1283-1284.
Lederman et al. "Preventing Coronary Obstruction During Transcatheter Aortic Valve Replacement," JACC Cardiovascular Interventions, Jul. 2019, vol. 12, No. 13, pp. 1197-1216.
Lisko et al. "Pachyderm-shape guiding catheters to simplify Basilica leaflet traversal," Cardiovascular Revascularization Medicine, Sep. 2019, vol. 20, No. 9, pp. 782-785.
Lisko et al. "Electrosurgical Detachment of MitraClips From the Anterior Mitral Leaflet Prior to Transcatheter Mitral Valve Implantation," JACC: Cardiovascular Interventions, Oct. 2020, vol. 13, No. 20, pp. 2361-2370.
Extended Search Report for European Patent Application No. 19756527.8, dated Oct. 18, 2021 9 pages.
Official Action with English Translation for China Patent Application No. 201980008535.4, dated Oct. 30, 2023 20 pages.

\* cited by examiner

FIG. 1A
FIG. 1B
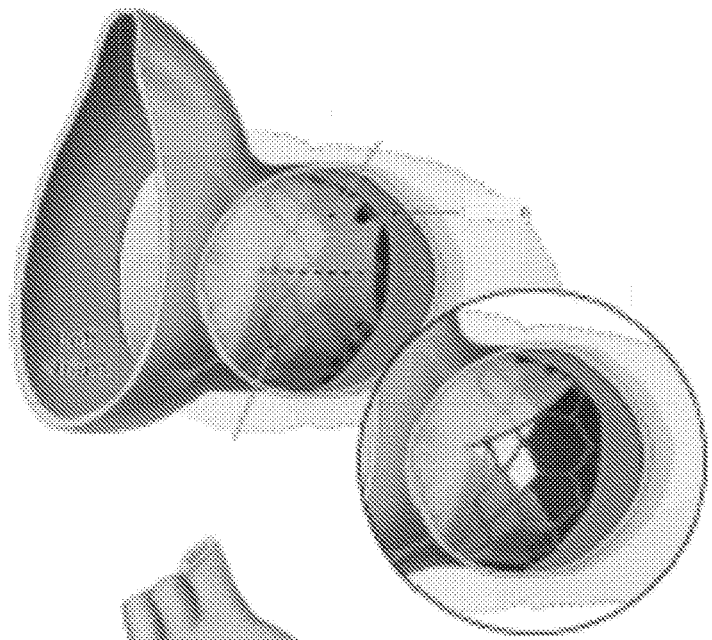
FIG. 1C
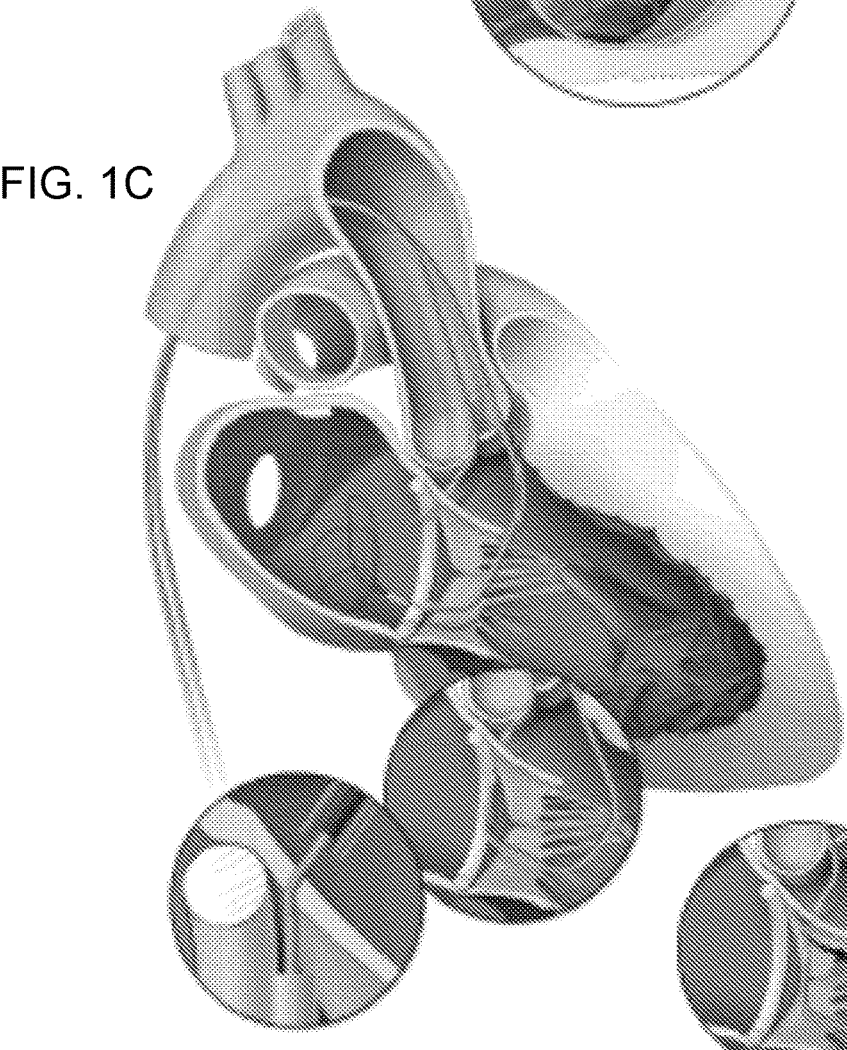
FIG. 1D
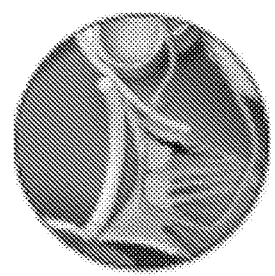
FIG 1E

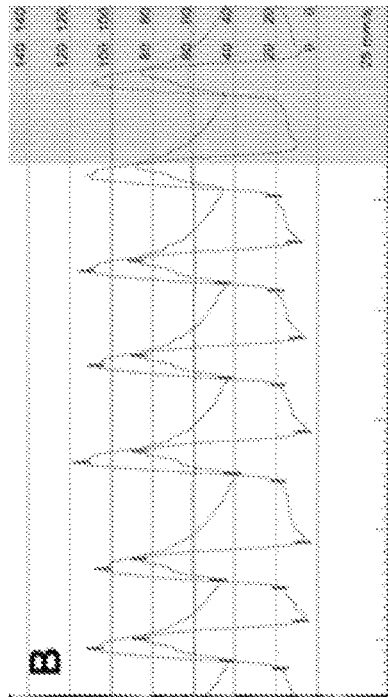
FIG. 3B
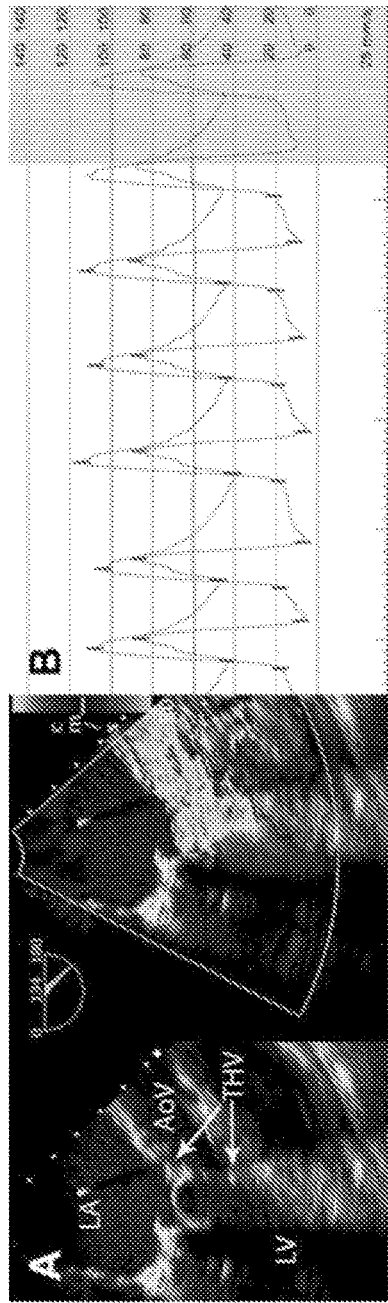
FIG. 3A
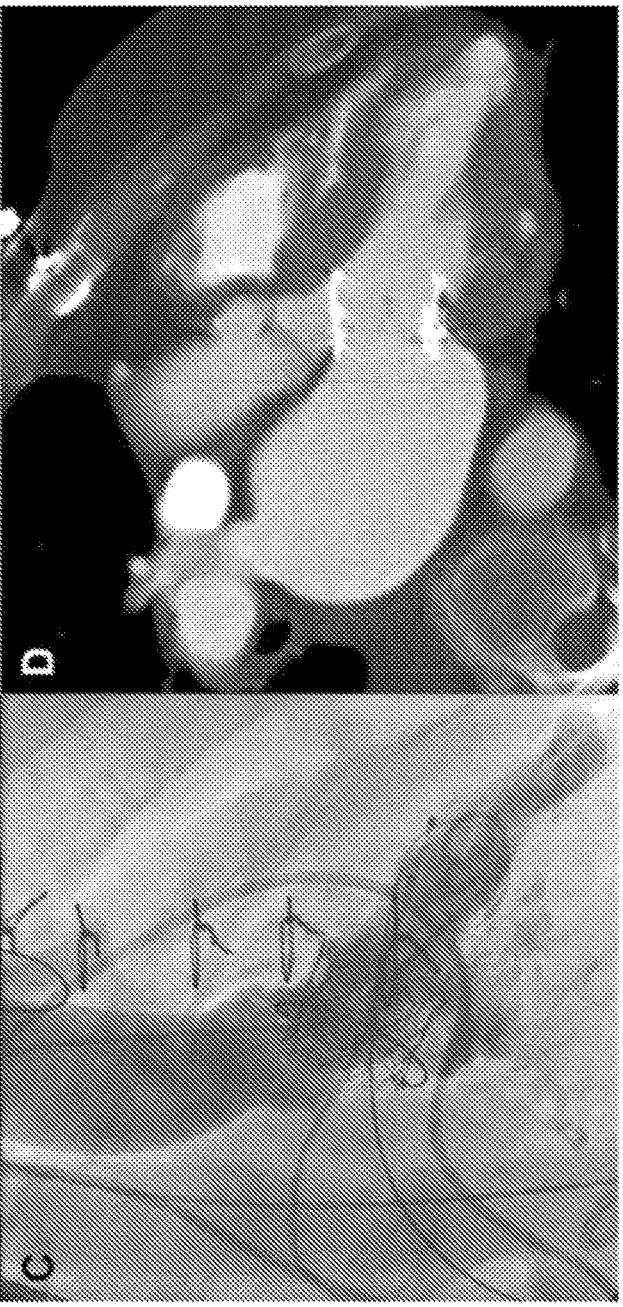
FIG. 3D
FIG. 3C

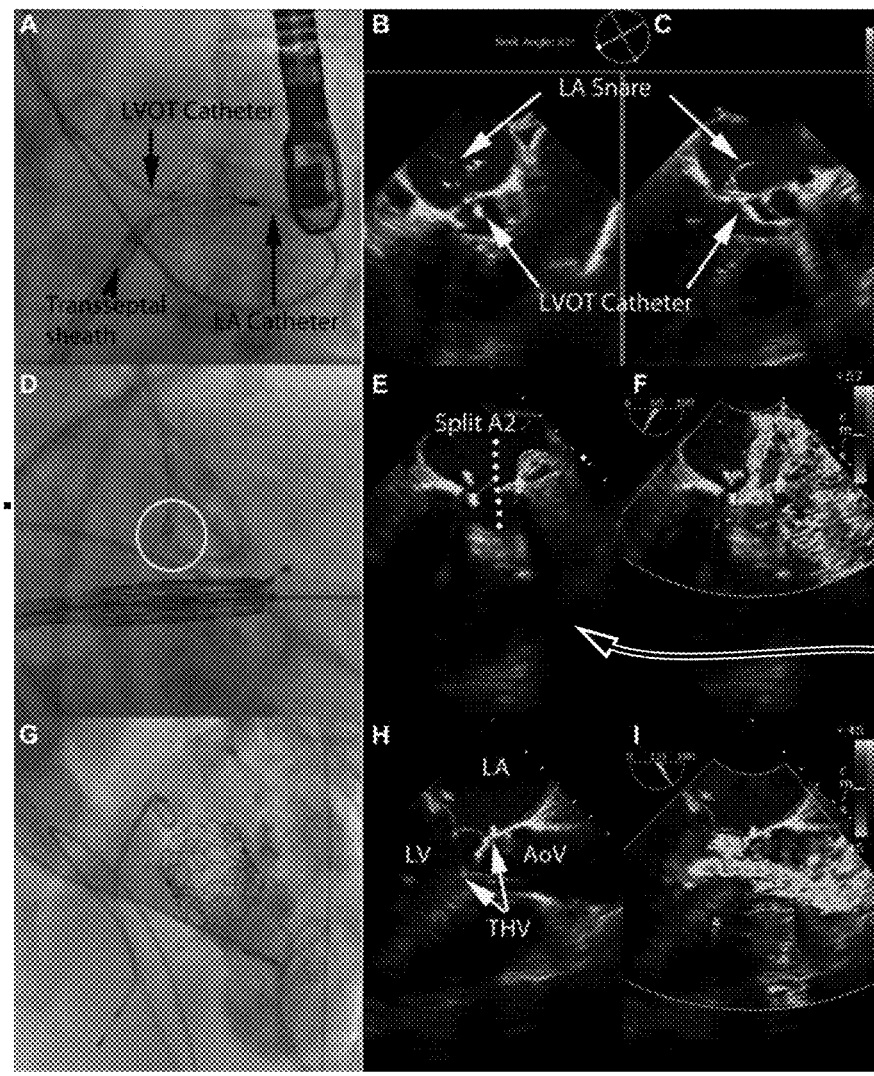

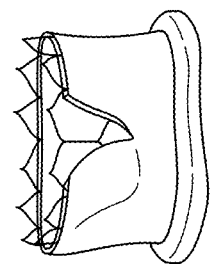
FIG. 9A
FIG. 9B
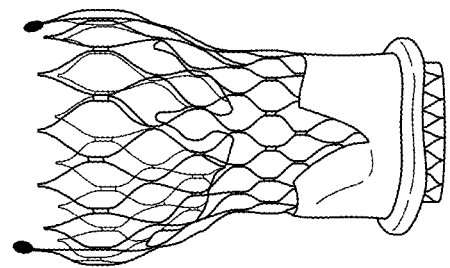
FIG. 9C
FIG. 9D

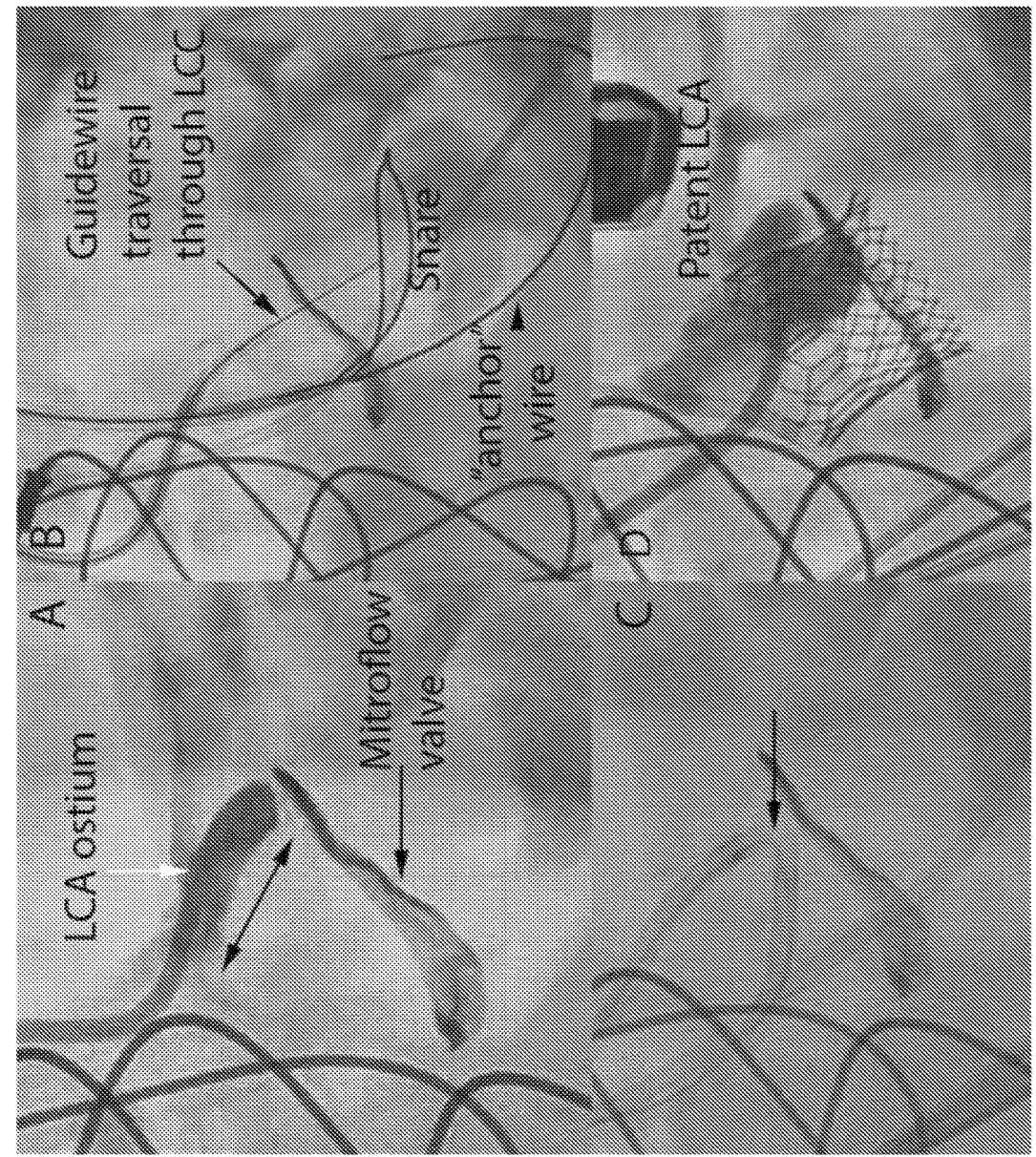

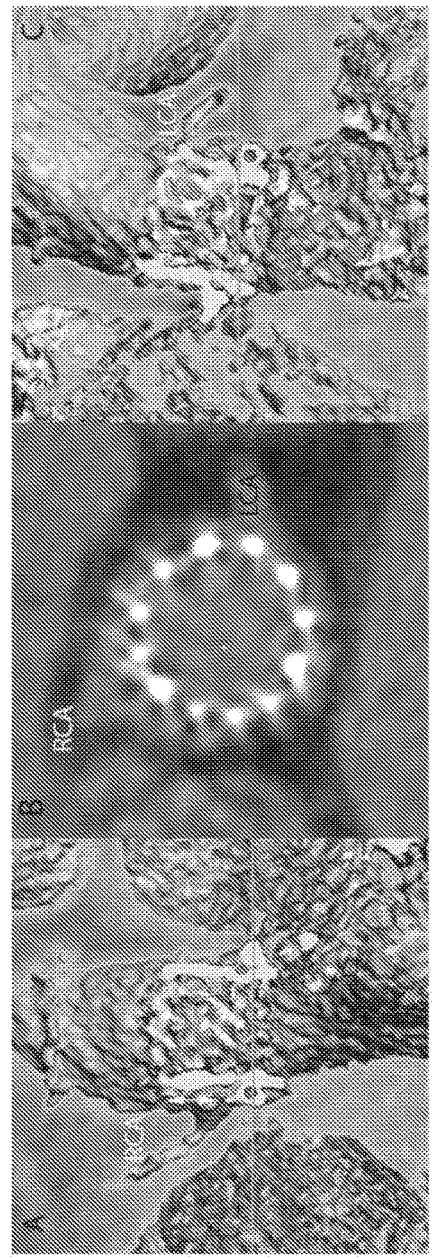
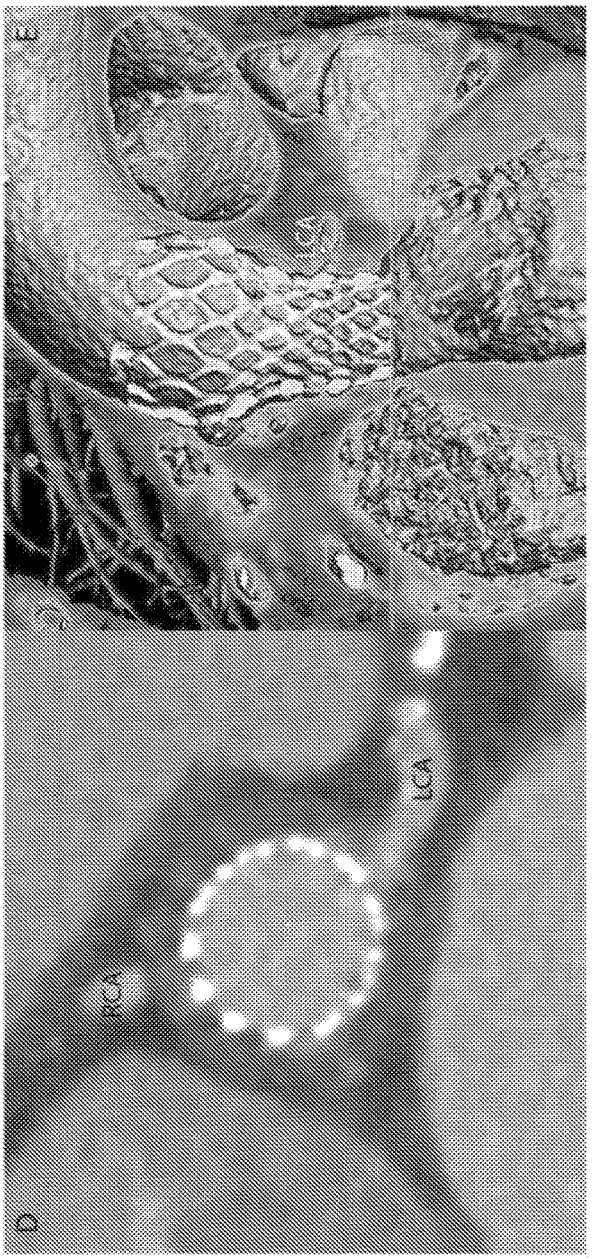
FIG. 15A  FIG. 15B  FIG. 15C  FIG. 15D  FIG. 15E

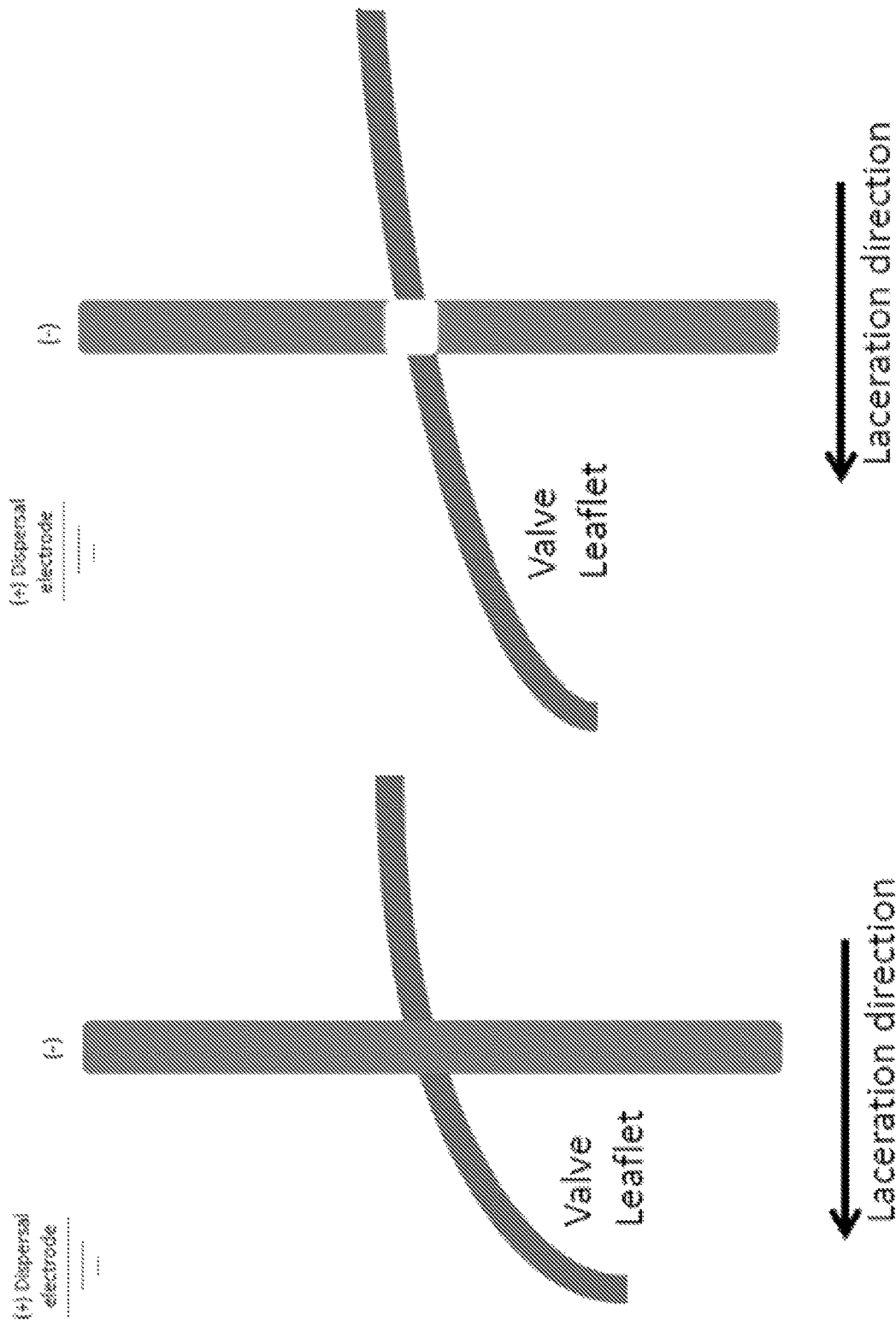

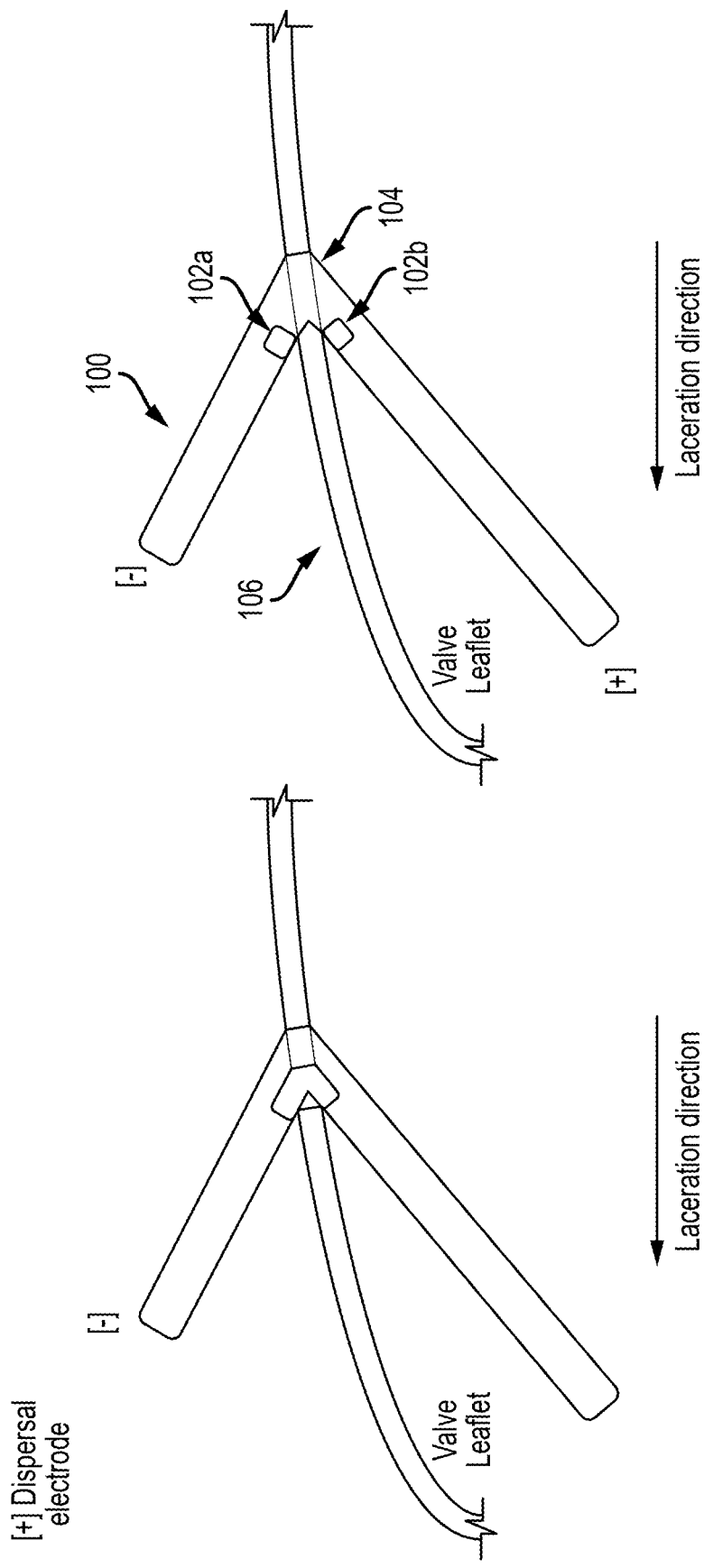

INNER CURVATURE CHARGE CONCENTRATION DEVICE FOR TISSUE LACERATION

CROSS-REFERENCE TO RELATED APPLICATIONS

This application is the U.S. National Stage of International Application No. PCT/US2019/018503, filed on Feb. 19, 2019, which claims the benefit of U.S. Provisional Application No. 62/633,791, filed on Feb. 22, 2018, which is incorporated by reference herein in its entirety.

FIELD

This disclosure is related to tissue laceration using electrical energy, such as for laceration heart valve leaflets.

BACKGROUND OF THE INVENTION

Heart valve leaflets can obstruct desired blood flow in some circumstances, such as when a leaflet is pushed into an open position by the implantation of a prosthetic heart valve within another valve. Thus, there is a need in the field for a solution to avoid such obstructions.

BRIEF SUMMARY OF THE INVENTION

Disclosed monopolar and bipolar tissue lacerators can comprise a wire partially covered by electrical insulation, wherein the wire has a kink defining an inner curvature, wherein the wire is exposed through the insulation at one or two exposed regions along or near the inner curvature of the kink, wherein the wire is configured to conduct electrical energy through the one or two exposed regions and through a tissue target positioned adjacent the inner curvature to lacerate the tissue target via the electrical energy. The tissue target can be a native or prosthetic heart valve leaflet in a patient's heart.

An irrigation catheter can also be used to inject a non-ionic liquid adjacent to the exposed portions of the lacerator to displace blood and reduce with electrical dissipation.

The disclosed lacerators can be used in various methods disclosed herein to lacerate heart valve leaflets within the heart, including at the aortic valve and at the mitral valve for example. Lacerating the leaflets can help prevent or reduce problems associated with the leaflets blocking desired blood flow, especially when a prosthetic heart valve is implanted within a native heart valve or within another prosthetic heart valve.

The foregoing and other features and advantages of the disclosed technology will become more apparent from the following detailed description of several embodiments which proceeds with reference to the accompanying figures.

BRIEF DESCRIPTION OF THE SEVERAL VIEWS OF THE DRAWINGS

FIGS. 1A-1E are views of the anterior mitral valve leaflet from the left ventricular outflow tract (LVOT). FIG. 1A: In this example, transcatheter mitral valve implantation displaces the native anterior mitral valve leaflet causing LVOT obstruction. FIG. 1B: After intentional Laceration of the Anterior Mitral leaflet to Prevent left ventricular Outflow Obstruction ("LAMPOON"), LVOT obstruction is reduced and blood flows across the unobstructed struts of the implanted transcatheter heart valve. FIGS. 1C-1E: Illustration of the LAMPOON procedure. FIG. 1C: retrograde guiding catheters are positioned across the aortic valve into the LVOT and another across the mitral valve into the left atrium. The LVOT catheter directs an electrified guidewire across the base of the anterior mitral valve leaflet under echocardiographic guidance into a snare positioned through the left atrial guiding catheter. FIG. 1D: Once the guidewire traverses the mitral leaflet, it is ensnared and externalized. The inset depicts a kinked section of the guidewire shaft that is denuded along its inner curvature to direct electrosurgery energy to the nearby leaflet. FIG. 1E: The guidewire is electrified and the guiding catheters withdraw it to lacerate the anterior mitral leaflet lengthwise.

FIG. 2A: Left anterior oblique caudal short-axis fluoroscopic projection showing retrograde catheters positioned before anterior mitral valve leaflet traversal. The retrograde LVOT and LA catheters overlap in this view, as intended. The posterior mitral valve band provides a fluoroscopic marker to position the LVOT catheter along the base of the A2 scallop. The LA catheter is directing the multiloop snare and is supported by a transseptal rail through a transseptal sheath. FIG. 2B: A 3-dimensional transesophageal echocardiograph of the same step, with a LVOT catheter positioned at the base of the A2 scallop, and the LA catheter pointing a multiloop snare at the other side of the A2 scallop. FIG. 2C: Initiation of laceration. The kinked guidewire cutting edge is circled in green. The transcatheter heart valve is pre-positioned at the orifice of the mitral valve. The LAMPOON guidewire is pulled outward to apply tension. FIG. 2D: The LAMPOON guidewire is electrified during further pulling to initiate laceration. FIG. 2E: Completed laceration, with both retrograde catheters insulating the wire safely in the descending aorta. The kinked guidewire cutting edge, adjacent to the radiopaque piggyback tip marker, is seen sheathed in the catheter.

FIGS. 3A-3D are imaging immediately after LAMPOON for transcatheter mitral valve replacement (TMVR)-in-Band. FIG. 3A: B-mode and color Doppler transesophageal echocardiography after LAMPOON and TMVR shows the stent struts protruding into the LVOT, and blood flow across those struts indicating successful leaflet splitting. FIG. 3B: Catheter pressure measurements across the LVOT show a tolerable gradient of 16 mm Hg. FIG. 3C: Left ventriculography, and FIG. 3D: contrast computed tomography after TMVR shows the THV encroaches completely across the LVOT and would nearly completely obstruct it if not for LAMPOON.

FIGS. 4A-4I illustrate LAMPOON to enable TMVR in native mitral annular calcification. FIGS. 4A-4C: Leaflet traversal, FIGS. 4D-4F: leaflet laceration, and FIGS. 4G-4I: imaging after LAMPOON and TMVR. (FIG. 4A: Guidewire traversal across the base of the anterior mitral leaflet. Four catheters are in place. An antegrade transseptal sheath, used for TMVR, is currently connected via a guidewire rail to control the retrograde LA catheter, which is used to deliver the multiloop snare on the LA side of the anterior mitral leaflet. A retrograde catheter in the LVOT is directing the traversing guidewire. There also is a pigtail catheter in the ascending aorta. FIGS. 4B, 4C: X-plane TEE immediately after leaflet traversal shows the mid-basal A2 position of the traversal system. Also evident are the 2 catheters and the LA snare. FIG. 4D: The traversing guidewire tip has been externalized. The guidewire shaft is denuded, kinked, and exposed between the 2 catheters (green circle), and is electrified to slice the anterior mitral leaflet longitudinally.

The THV is prepositioned for immediate deployment. FIGS. 4E, 4F: B-mode and color Doppler TEE after LAMPOON but before TMVR shows severe acute mitral valve regurgitation across the split A2 leaflet scallop. FIG. 4G: Left ventriculography after TMVR shows the THV encroaches nearly completely across the LVOT and would nearly completely obstruct it if not for LAMPOON. FIGS. 4H, 4I: B-mode and color Doppler TEE after LAMPOON and TMVR shows the stent struts protruding into the LVOT and blood flow across those struts indicating successful leaflet splitting.

" FIG. 5A: A laceration cleft is evident (dotted green line) at the beginning of diastole in the A2 scallop of the anterior mitral leaflet. FIG. 5B: The medial half of A2 and the whole of A3 open early in diastole and then FIG. 5C: the lateral half of A2 along with the whole of A1 open a fraction later in diastole. A1 to A3 and P1 to P3 represent the lateral to medial scallops of the anterior and posterior mitral leaflets, respectively.

FIGS. 7A-7C: In normal transcatheter aortic valve replacement (TAVR) performed in a capacious aortic root, blood flows unrestricted around valve leaflets into coronary arteries. In patients with a crowded sinus and low lying coronary arteries, coronary blood flow is obstructed by the bioprosthetic valve leaflets after TAVR. After BASILICA, blood flows through the open cells of the transcatheter heart valve unimpeded into the coronary artery.

FIG. 8A illustrates a catheter directing an electrified guidewire through the base of the left aortic cusp into a snare in the left ventricular outflow tract. FIG. 8B: after snare retrieval, the mid-shaft of the guidewire is electrified to lacerate the leaflet FIG. 8C. FIG. 8D: the leaflet splays after TAVR permitting coronary flow.

FIGS. 9A-9D illustrate a benchtop simulation of BASILICA. FIGS. 9A-9D: Two different transcatheter heart valves (23 mm Sapien 3, top, and 26 mm Evolut Pro, bottom) implanted in 25 mm Mitroflow before (left) and after (right) the leaflet is cut with a scalpel.

FIGS. 11A-11D illustrate BASILICA for TAVR with S3 in failed Mitroflow valve. FIG. 11A: left coronary injection demonstrates a high risk of left coronary obstruction from the Mitroflow leaflet (double headed arrow). FIG. 11B: Co-axial catheters direct an electrified guidewire through the left coronary leaflet of the Mitroflow valve into the left ventricular outflow tract snare. FIG. 11C: laceration with radiofrequency concentrated at the kinked mid-shaft of the Astato guidewire (arrow). FIG. 11D: left cusp injection with flow through split leaflet and patent left coronary artery that would otherwise have been obstructed. LCA=left coronary artery; LCC=left coronary cusp.

FIG. 12A: An electrified guidewire traverses native left coronary cusp leaflet into the LVOT snare. FIG. 12B: leaflet laceration through exposed kinked guidewire shaft (arrow). FIG. 12C: aortic root angiography showing coronary flow in a low lying coronary artery that may have been obstructed without BASILICA.

FIG. 13A: Heavily calcified leaflets, especially the left coronary cusp. FIG. 13B: Left coronary height is low at 3.4 mm. FIG. 13C: Both left and right VTC (virtual transcatheter valve to coronary distance) are low at 3.3 mm. FIG. 13D: An electrified guidewire traverses the left coronary leaflet of a *Magna* valve. FIG. 13E: The left coronary leaflet guidewire has been externalized to form a loop and a second electrified guidewire traverses the right coronary leaflet. FIG. 13F: Loops formed around both left (white arrow) and right (black arrow) coronary cusps, ready for sequential laceration. FIG. 13G: After TAVR a high pressure balloon is inflated to crack the bioprosthetic valve to improve hemodynamics. FIG. 13H: The bioprosthetic valve has been fractured at the site of the black arrow. FIG. 13I: angiography demonstrates good flow to both coronary arteries that may otherwise have been completely obstructed. LCC=left coronary cusp; RCC=right coronary cusp; NCC=non-coronary cusp; RCA=right coronary artery; LCA=left coronary artery; VTC=virtual transcatheter valve to coronary distance.

FIG. 14A: Echocardiography view showing the traversal catheter is aligned at the base of the left coronary cusp (upward arrow). A snare catheter is positioned across the valve (downward arrow). FIG. 14B: The laceration in the left coronary cusp is seen (arrow), adjacent to the left coronary artery ostium. LCA=left coronary artery.

FIGS. 15A-15E illustrate CT images following BASILICA and TAVR with S3. FIGS. 15A-15B: A narrow neo-sinus (double-headed arrow) maintains flow to the right coronary artery but the left sinus, FIGS. 15B-15C: are completely effaced. FIGS. 15D-15E: The left coronary artery was at risk of occlusion but there is adequate filling following BASILICA.

FIG. 17 illustrates an insulated conductive wire lacerating a valve leaflet.

FIG. 18 illustrates a focally non-insulated conductive wire lacerating a leaflet.

FIG. 19 illustrates a kinked, monopolar, focally non-insulated lacerator.

FIG. 20 illustrates a kinked, bipolar, focally non-insulated lacerator.

DETAILED DESCRIPTION OF THE INVENTION

Figure 2A:
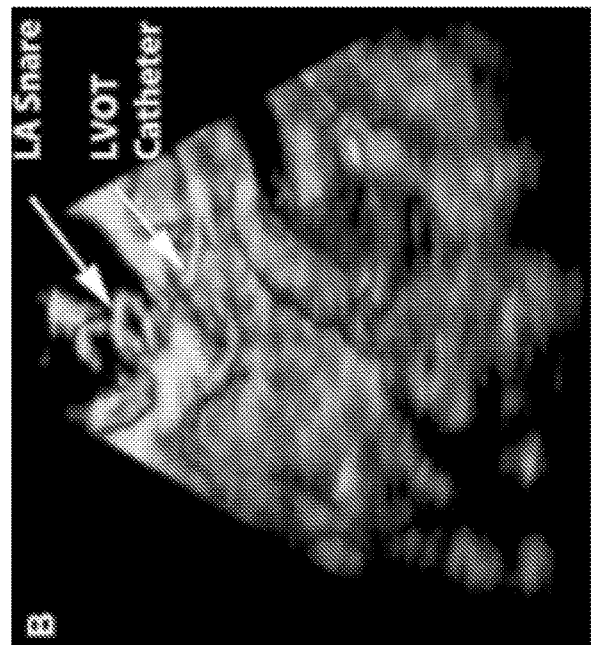
FIGS. 2A-2E show LAMPOON to enable transcatheter mitral valve replacement inside a flexible mitral annuloplasty band.

Intentional Percutaneous Laceration of the Anterior Mitral Leaflet to Prevent Outflow Obstruction During Transcatheter Mitral Valve Replacement Left ventricular outflow tract (LVOT) obstruction is a life-threatening complication of TMVR, caused by septal displacement of the anterior mitral leaflet (AML).

This study sought to use a new catheter technique to split the AML and prevent iatrogenic left ventricular outflow tract (LVOT) obstruction immediately before transcatheter mitral valve replacement (TMVR).

The procedure was used in patients with severe mitral valve disease and prohibitive surgical risk. Patients either had prior surgical mitral valve ring (n=3) or band annuloplasty (n=1) or mitral annular calcification with stenosis (n=1). Iatrogenic LVOT obstruction or transcatheter heart valve dysfunction was predicted in all based on echocardiography and computed tomography. Transfemoral coronary guiding catheters directed an electrified guidewire across the center and base of the AML toward a snare in the left atrium. The externalized guidewire loop was then electrified to lacerate the AML along the centerline from base to tip, sparing chordae, immediately before transseptal TMVR.

Five patients with prohibitive risk of LVOT obstruction or transcatheter heart valve dysfunction from TMVR successfully underwent intentional Laceration of the Anterior Mitral leaflet to Prevent left ventricular Outflow Obstruction ("LAMPOON"), with longitudinal splitting of the A2 scallop of the AML, before valve implantation. Multiplane computed tomography modeling predicted hemodynamic collapse from TMVR assuming an intact AML. However, critical LVOT gradients were not seen following LAMPOON and TMVR. Doppler blood flow was seen across transcatheter heart valve struts that encroached the LVOT, because the AML was split. Transcatheter heart valve function was unimpeded.

This novel catheter technique, which resembles surgical chord-sparing AML resection, may enable TMVR in patients with prohibitive risk of LVOT obstruction or transcatheter heart valve dysfunction.

The anterior mitral valve leaflet (AML) is a mobile structure that physically separates inflow and outflow zones of the left ventricle. Preserving the AML during surgical mitral valve replacement can cause left ventricular outflow tract (LVOT) obstruction, either when the prosthesis struts protrude into the LVOT or when along redundant anterior leaflet prolapses into the LVOT. In a similar manner, implantation of a transcatheter heart valve (THV) inside the native or repaired mitral valve enforces an "open position" of the AML that may encroach on the LVOT. This septal displacement of the AML is exaggerated when the aortic and mitral annular planes are acutely angulated rather than parallel, when the interventricular septum bulges toward the LVOT, when the AML is elongated, and when the implant extends or flares into the left ventricle. In this setting transcatheter mitral valve replacement (TMVR) may cause life-threatening LVOT obstruction. Moreover, after TMVR an excessively long AML may prolapse anteriorly into a narrowed LVOT as in hypertrophic cardiomyopathy, or it can prolapse posteriorly and interfere with bioprosthetic heart valve opening or closing by mechanical or Bernoulli effects after surgical or transcatheter mitral replacement. Longer AMLs are more susceptible to these effects. Although few data are available to guide decision-making, one-half of TMVR candidates having an intact AML are excluded from an ongoing clinical investigation because of the perceived risk of life-threatening LVOT obstruction.

One approach to prevent or treat TMVR-related LVOT obstruction is pre-emptive transcoronary alcohol septal ablation, which sacrifices myocardium and risks conduction system injury and pacemaker-dependence in patients with cardiomyopathy, which is unsuitable in patients with thin interventricular septa, and which delays TMVR by 4 to 6 weeks to allow remodeling in highly symptomatic patients.

Another option is surgical AML resection combined with TMVR during thoracotomy and cardiopulmonary bypass, with attendant risk and morbidity to patients already believed to be at high risk for cardiac surgery.

As an alternative, we have developed a transcatheter adjunct to TMVR using off-the-shelf equipment, and described its preclinical use. This technique resembles David's surgical anterior resection with chordal sparing. We create a longitudinal split of the middle scallop (A2) of the AML, immediately before TMVR. As a result, chordal attachments displace the split AML away from the LVOT after the cylindrical THV is implanted, and blood flows unobstructed across the THV stent struts.

We report the initial human experience with this intentional laceration of the AML to prevent left ventricular outflow tract obstruction (LAMPOON) procedure.

TMVR with LAMPOON was performed at 2 medical centers, Emory University Hospital and Henry Ford Hospital. The institutional ethics review boards of both approved this communication. Five patients deemed inoperable and believed to have prohibitive risk of TMVR because of intact native mitral leaflets consented explicitly to this novel procedure, as clinical therapy, after consensus from the local multidisciplinary structural heart teams.

Baseline electrocardiogram-gated contrast-enhanced 64-detector row cardiac computed tomography (CT) angiography was obtained to measure annular and/or annuloplasty dimensions to select a THV. Multiplanar reconstruction (Vitrea, Toshiba, Tustin, California) was performed to predict the following working projections: angle of TMVR deployment perpendicular to the prosthesis or annulus, a left anterior oblique caudal projection corresponding to a short-axis CT reconstruction to depict LAMPOON traversal position along the medial-lateral dimension, and an attainable right anterior oblique caudal projection corresponding to a 3-chamber CT reconstruction to depict LAMPOON traversal position along the leaflet base-to-tip dimension.

A predicted post-TMVR minimum LVOT area ("threatened neo-LVOT") area was obtained on a separate workstation (Mimics, Materialise, Leuven, Belgium). TMVR was simulated in systole using cylinders corresponding to the known external length and diameter of the planned THVs, implanted at the intended depth relative to the mitral annulus (80/20 left ventricle/left atrium [LA]), and the minimum projected area recorded assuming the AML would be obstructive only where it contacts the TMVR device.

AML lengths were measured on CT and trans-esophageal echocardiography (TEE). Long leaflet length (>30 mm, compared with nominal height 18.0 to 22.5 mm of Sapien 3, Edwards Lifesciences, Irvine, California) combined with acute aortomitral angle, was considered an independent risk factor for LVOT obstruction and THV dysfunction as part of the multidisciplinary heart team evaluation, accepting the difficulty modeling this based on static CT images. TMVR with LAMPOON was performed in a biplane angiography system at one site, and single plane in the other. All patients underwent general anesthesia and intraprocedural TEE.

The LAMPOON procedure comprises three steps: leaflet traversal with a guidewire, followed by leaflet laceration, immediately followed by TMVR. These are all guided by fluoroscopy combined with TEE.

For leaflet traversal, 2 6-F coronary guiding catheters (JL3.5) are advanced across the aortic valve through 2 femoral artery sheaths. One guiding catheter is positioned retrograde in the LVOT abutting the base of A2 to direct the traversal guide-wire, and the other retrograde into the LA across the aortic and mitral valves.

In patients with mitral stenosis, we found it helpful to advance the retrograde LA catheter over a 0.014 wire rail into the transseptal catheter. The rail eases LA catheter repositioning should it prolapse into the left ventricle. The rail is formed by advancing a balloon tip catheter from a transseptal deflectable catheter (*Agilis* NXT medium curl, St. Jude Medical, St. Paul, Minnesota) in the LA through the main orifice of the mitral valve. The rail is a kink-resistant guidewire (Runthrough NS 0.014-inch, Terumo Interventional Systems, Somerset, New Jersey), and is externalized after snaring. Through the retrograde LA catheter, a multi-loop snare (Atrieve 18/30, Argon Medical, Plano, Texas) is positioned alongside the rail and alongside the mitral coaptation surfaces.

The electrosurgical traversal technique is derived from the technique of transcaval crossing. The traversal guidewire is a 0.014-inch×300 cm guidewire (Astato XS 20, Asahi Intecc USA, Santa Ana, California) inside an insulating polymer jacket wire convertor (Piggyback, Teleflex Vascular Solutions, Minneapolis, Minnesota), inside the retrograde LVOT guiding catheter. The external back end of the guidewire is connected via hemostatic forceps to an electrosurgery pencil and generator (ValleyLabFX, Medtronic Covidien, Minneapolis, Minnesota), set to "pure" cutting mode at 50 W. The traversal guidewire is advanced from the LVOT catheter, penetrating the base of the A2 scallop, during brief (<1 s) electrification into the prepositioned left atrial snare. The wire is captured and externalized through the retrograde LA catheter.

The marketed guidewire shaft is coated with an insulating polymer. A short segment along the middle of the guidewire shaft is noncircumferentially denuded of its polymer insulation, and then kinked, using a scalpel. This modification focuses electrosurgery energy required for laceration on the inner curvature of the guidewire. The radiopaque tip of the Piggyback wire converter is locked behind the denuded kinked segment, because it provides additional insulation and because it positions a radiopaque marker adjacent to the kinked and denuded lacerating surface. The kinked segment is positioned to straddle the AML.

For laceration, both free guidewire ends are firmly pulled during electrification in a series of brief (<1 s) steps. Pulling the guidewires helps to oppose the guiding catheters, to protect the aortic valve, and to initiate laceration at the base of the AML (see, e.g., FIG. 1E). Further tension on the guidewires completes the splitting of the AML.

TMVR was performed via an antegrade transseptal route using Edwards Sapien 3 devices. The rigid TMVR guidewire was delivered into the left ventricle after first crossing the major mitral orifice using a balloon wedge endhole catheter, and atrial septostomy performed using 12-to-16-mm balloon dilatation catheters to ensure transseptal THV delivery. Tension was applied to the LAMPOON catheter system under fluoroscopy to ensure the TMVR guidewire was not entrapped. The THV was positioned in the left atrium or partway across the mitral valve before LAMPOON laceration to facilitate rapid deployment in case of early hemodynamic compromise.

TMVR was performed immediately after LAMPOON, using rapid right ventricular pacing and slow balloon inflation. After the first inflation, the THV delivery balloon was advanced slightly forward and reinflated with at least 4 ml additional inflation volume to flare the ventricular aspect of the THV stent. At the conclusion of the procedure, the iatrogenic atrial septal defect was closed based on operator discretion.

Post-procedure invasive pressure and Doppler echocardiography gradients were recorded across the LVOT and THV, using peak-to-peak and peak-instantaneous measurements for hypertrophic cardiomyopathy. Post-procedure neo-LVOT was evaluated by echocardiography. TMVR encroachment on the LVOT was measured in B-mode to determine the retrospective "threatened" LVOT diameter as if LAMPOON had not been performed, and in color Doppler mode to visualize blood flow across the THV stent struts and determine the "actual" LVOT diameter. Similarly, post-procedure CT was evaluated to measure a "threatened" LVOT area as if LAMPOON had not been performed. Data were reported as mean±SD or as median (range) as appropriate.

Clinical characteristics of the 5 patients are shown in Table 1 (below). All were believed to have prohibitive surgical risk and no therapeutic alternatives. None were considered suitable for preparatory alcohol septalablation to debulk the LVOT.

The first 4 patients had undergone prior surgical mitral annuloplasty. The first had a rigid annuloplasty ring (primarily regurgitant lesion), the next 2 had semi-rigid rings (1 primarily stenotic and the other mixed regurgitant/stenotic), the fourth had a flexible posterior annuloplasty band (primarily stenotic), and modeling. One required intra-aortic balloon pump at baseline because of intractable heart failure. No others required mechanical circulatory support.

TABLE 1

| Baseline Clinical Characteristics (n = 5) | |
| --- | --- |
| Age, yrs | 64.8 ± 13.2 |
| Female, % | 40 |
| Severe pulmonary disease, % | 60 |
| Prior stroke, % | 40 |
| Atrial fibrillation, % | 60 |
| eGFR ml/min/1.73 m$^2$ | 65.4 ± 11.4 |
| NT-proBNP baseline | 432.3 ± 346.9 |
| STS PROM mitral valve replacement, % | 8.2 ± 3.6 |
| NYHA CHF functional class | 3.8 ± 0.4 |
| TMVR setting | TMVR-in-ring = 3 |
|  | TMVR-in-band = 1 |
|  | TMVR-in-MAC = 1 |
| Primary lesion (valvular stenosis/regurgitation/mixed) | 3/1/1 |
| Ring or band nominal diameter, mm | 30.0 ± 2.8 |
| Left ventricular ejection fraction | 0.48 ± 0.14 |
| Right ventricular dysfunction, % | 80 |
| Echo septal thickness, mm | 8.8 ± 1.1 |
| Echo septal thickness amenable to alcohol septal ablation, % | 0 |

Values are mean ± SD or %.
CHF = congestive heart failure; eGFR = estimated glomerular filtration rate; MAC = mitral annular calcification; NT-proBNP = N-terminal pro-B-type natriuretic peptide; NYHA = New York Heart Association; STS PROM = Society of Thoracic Surgeons predicted risk of mortality; TMVR = transcatheter mitral valve replacement.

| Procedure Chartacteristics, Hemodynamics, and Imaging (n = 5) | |
| --- | --- |
| TMVR size, Sapien 3, mm | 26 (n = 2); |
|  | 29 (n = 3) |
| Crossing power, W | 50 ± 0 |
| Lacerating power, W | 58 ± 11 |
| LVOT catheter Judkins left length, cm | 3.9 ± 0.7 |
| Left atrial retrograde catheter Judkins left length, cm | 3.7 ± 0.3 |
| Procedure time, min | 214 ± 24 |
| Time from catheter to valve, min | 133 ± 19 |
| Time from leaflet traversal to leaflet laceration, min | 66 ± 10 |

-continued

Procedure Chartacteristics,
Hemodynamics, and Imaging (n = 5)

| Time from laceration to TMVR, min (range) | 3.0 (1-38) |
|---|---|
| Fluoroscopy time, min | 116 ± 39 |
| Radiation dose-area product, Gy · cm² | 335 ± 319 |
| Contrast volume, ml | 68 ± 41 |
| Iatrogenic atrial septal defect closed | 4 of 5 |

| Pressure, mm Hg | Before | After |
|---|---|---|
| Mitral valve gradient mean | 9.2 ± 4.2 | 4.6 ± 4.0 |
| LVOT gradient (range) | 7.4 ± 0.5 (7-8) | 17.6 ± 12.4 (8-39) |
| LA mean pressure | 25.8 ± 9.2 | 18.2 ± 4.8 |
| LA v-wave | 50.2 ± 15.9 | 30.0 ± 6.4 |
| PA systolic pressure | 72.8 ± 10.9 | 58.2 ± 15.4 |

Computed Tomography Characteristics

| Aortomitral plane angle, degrees, n = 5 | 123 ± 10 |
|---|---|
| Neo-LVOT* predicted, mm², n = 2 | 67 ± 4 |
| Neo-LVOT* after TMVR, mm², n = 2, assuming LAMPOON had not been performed | 50 ± 71 |

Echo Characteristics After TMVR

| LVOT max native dimension B-mode after TMVR, mm | 17.6 ± 2.1 |
|---|---|
| LVOT vena contracta after TMVR (includes stent-free), mm | 11.8 ± 3.5 |
| LVOT stent-free length after TMVR, mm | 4.4 ± 4.5 |
| LVOT obstruction threatened diameter, † % | 76 ± 24 |
| LVOT obstructed actual diameter, % | 34 ± 15 |
| LVOT gradient peak-instantaneous by echo, pre-discharge, mm Hg | 26 ± 11 |
| LVOT gradient peak-instantaneous by echo, 1 month, mm Hg | 17 ± 10 |

Values are mean ± SD (range). *Neo-LVOT is the minimum cross-sectional area of the LVOT expected after implantation of the selected valve, based on 3-dimensional computed tomography analysis. These assume there is no flow across the struts of the implanted transcatheter heart valve. Neo-LVOT is reported on the 2 patients with predicted stent encroachment rather than excessive anterior mitral valve leaflet length. †Threatened diameter refers to the diameter obstruction of the LVOT assuming there would be no flow across the struts of the transcatheter heart valve.
LA = left atrium; LAMPOON = laceration of the anterior mitral leaflet to prevent left ventricular outflow tract obstruction; LVOT = left ventricular outflow tract; PA = pulmonary artery; other abbreviations as in Table 1.

Figure 2B:
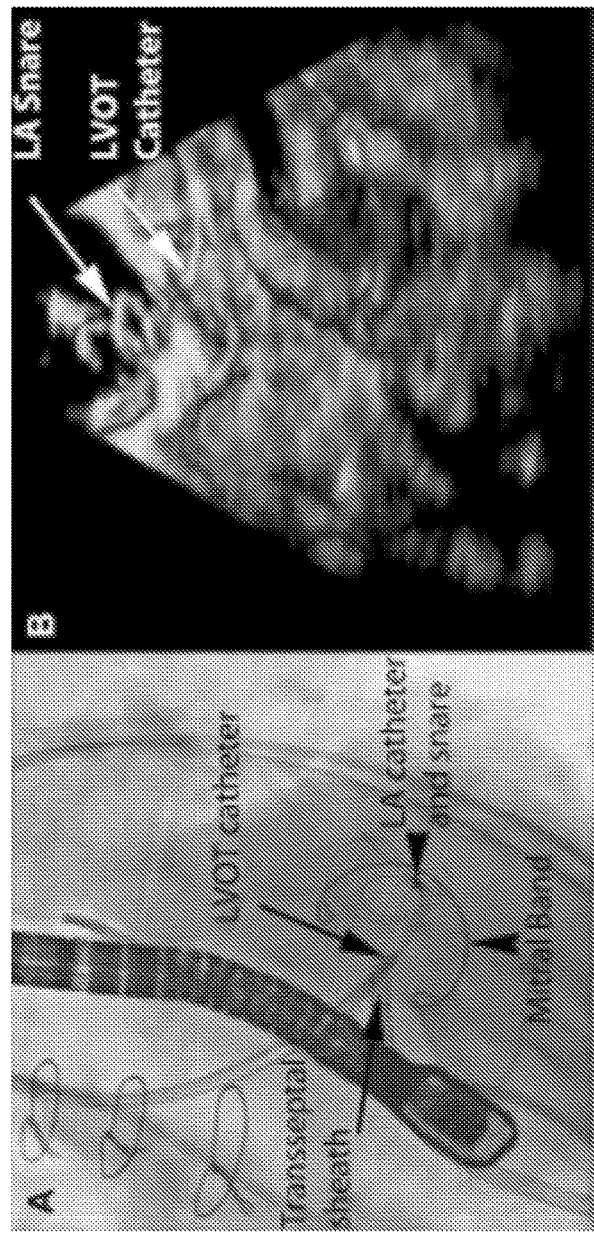
Figures 2C, 2D, 2E:
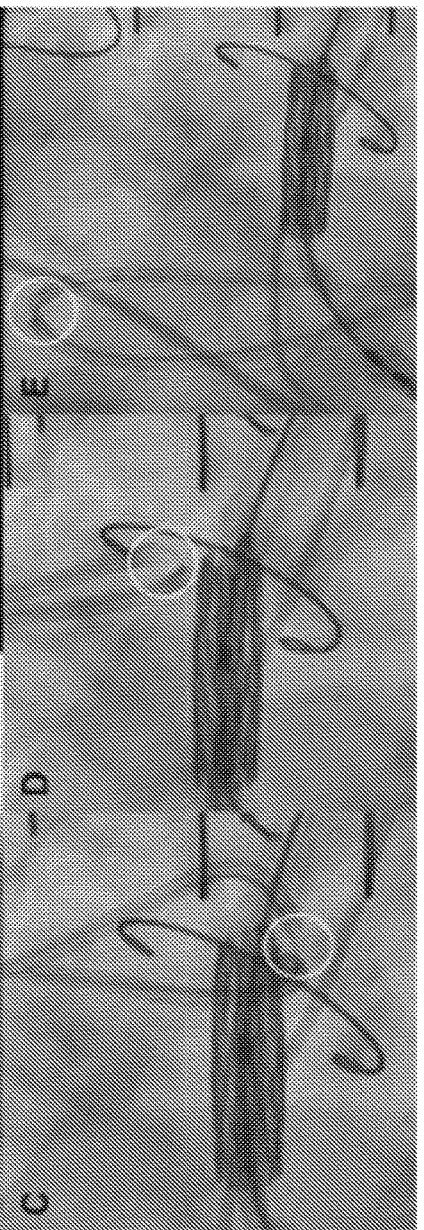
Figures 5A, 5B, 5C:
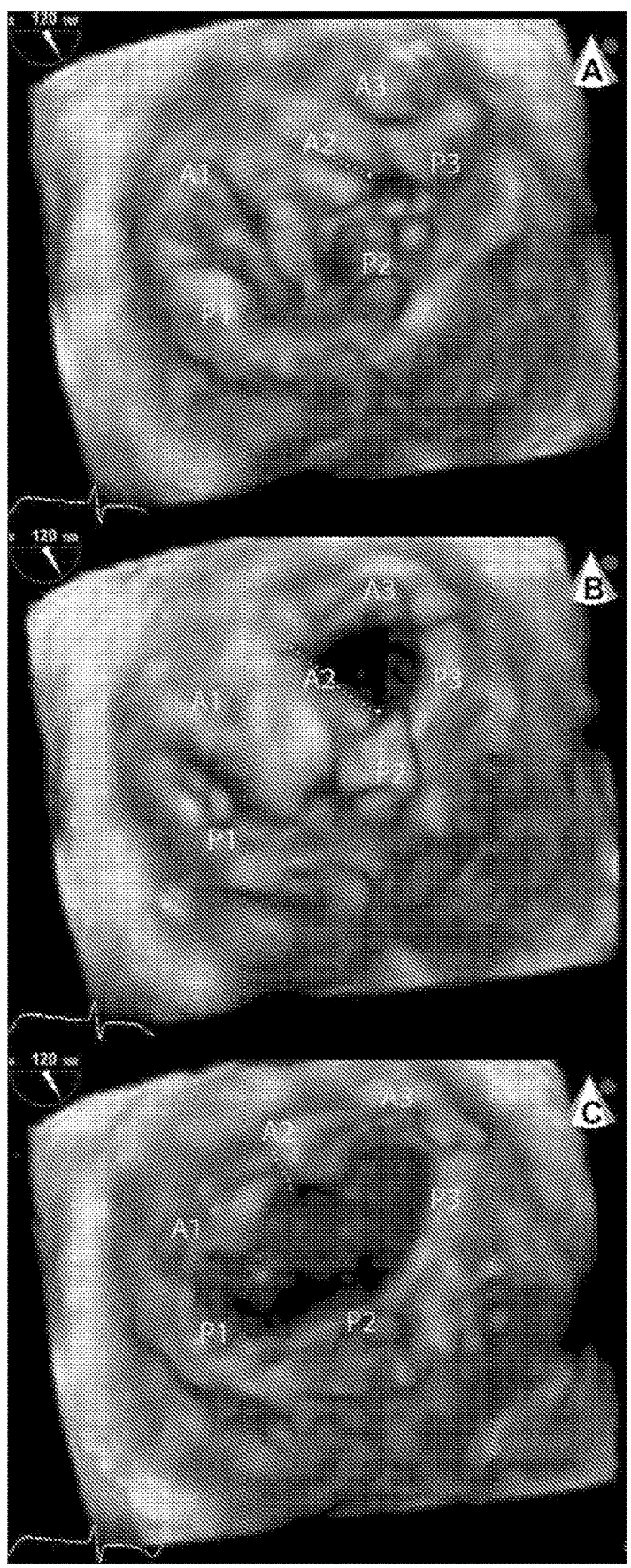
FIGS. 5A-5C illustrate LAMPOON induced anterior mitral leaflet split. Three sequential diastolic frames of a 3-dimensional echocardiogram performed immediately after LAMPOON but before TMVR. The volume is rendered from a left-atrial "surgeons view.
Figure 6A:
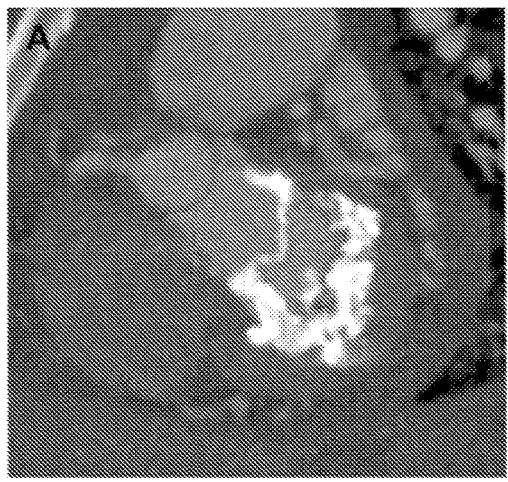
FIGS. 6A-6F illustrate LAMPOON and TMVR in mitral annular calcification. Computed tomography scans before FIGS. 6A-6C and after FIGS. 6D-6F TMVR with LAMPOON in a patient treated for mitral annular calcification causing mitral valve stenosis. Noncalcified fibrous valve tissue (asterisk) is interposed between the THV and the mitral annular calcification FIG. 6D. The transcatheter heart valve is shown to span across the LVOT FIG. 6E, suggesting there would have been complete LVOT obstruction had LAMPOON not been performed. Follow-up chest images FIG. 6F show near-resolution of pulmonary alveolar hemorrhage and pleural effusion.
Figure 6D:
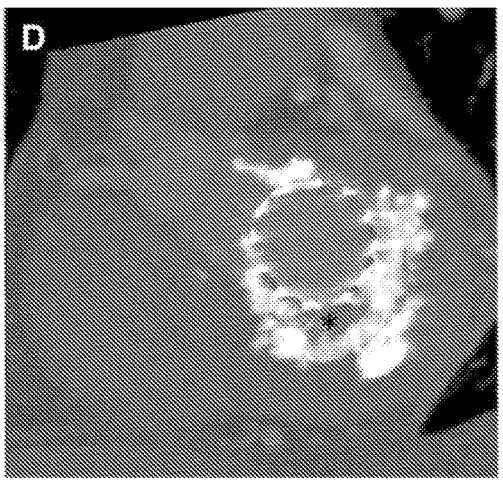
Figure 6B:
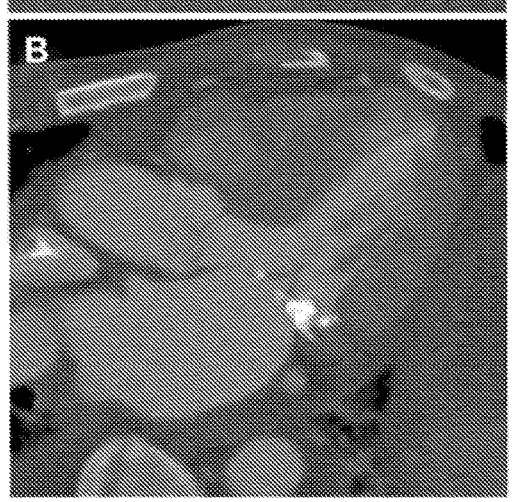
Figure 6E:
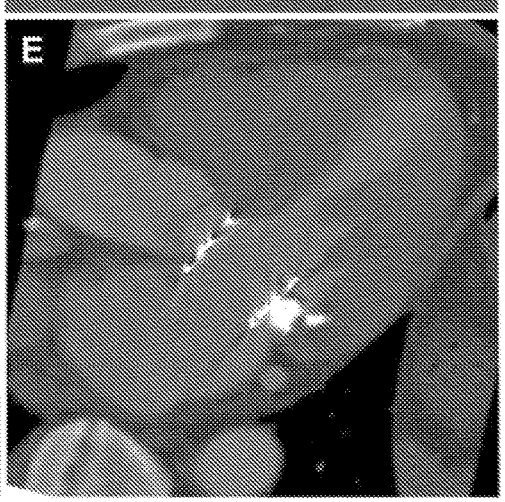
Figure 6C:
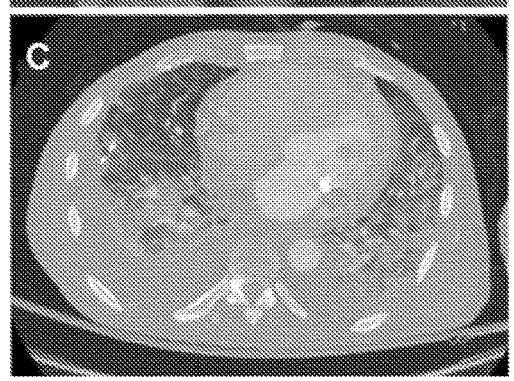
Figure 6F:
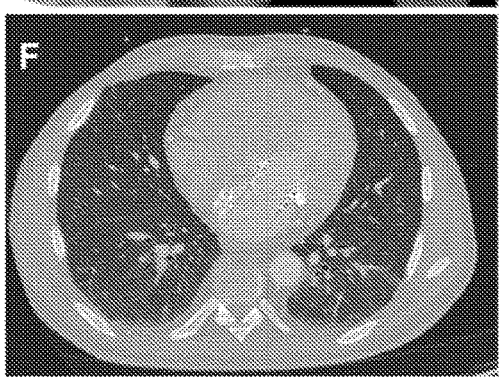

Procedure details are shown in Table 2 (above). A representative procedure is depicted in Online Video 2. Preparatory LAMPOON successfully split the A2 scallop of the AML in all 5 patients. FIGS. 2 and 3 show representative radio-graph, TEE, and CT images of a patient undergoing LAMPOON and TMVR after prior surgical mitral annuloplasty. FIG. 4 shows radiograph and TEE sequences of a patient undergoing LAMPOON and TMVR for MAC causing mitral stenosis. FIG. 5 shows the split mitral leaflet in the interval between LAMPOON and TMVR. FIG. 6 shows CT images of a patient treated for mitral stenosis caused by MAC, causing pulmonary alveolar hemorrhage. After TMVR with LAMPOON, the THV is seen spanning the entire LVOT, and the pleural and pulmonary abnormalities are dramatically improved.

The blood pressure and heart rate did not decline in any patient during the 1-to-38-min interval be-tween LAMPOON and TMVR. Hemodynamic details are shown in Table 2. The average post-procedure LVOT catheter gradient was 17.6×12.4 mm Hg immediately after LAMPOON and TMVR in these patients otherwise expected to have intolerable LVOT obstruction or THV dysfunction.

X-plane TEE guided medial-lateral and base-to-tip positioning of the LVOT catheter before and during leaflet traversal and laceration, complemented by left anterior oblique caudal short-axis and right anterior oblique caudal pseudo-3-chamber fluoroscopic projections. A true 3-chamber extreme left anterior oblique cranial or extreme right anterior oblique caudal projection was not attainable in any patient.

LAMPOON created a new jet of severe mitral regurgitation across the A2 scallop in all 5 cases. After TMVR, blood flow across the THV struts was evident from the left ventricular inflow into the LVOT, which would not have been possible if the AML had not been disrupted. Echocardiography and CT details are summarized in Table 2.

Four patients (80%) survived beyond 1 month (197 days [range 23 to 273 days] as of this report). Complications are described in Table 3. There were no procedural strokes, clinically significant paravalvular leaks, or major bleeding or vascular complications of the LAMPOON and TMVR procedure.

In the first patient, the THV embolized immediately into the left atrium. In retrospect it was significantly undersized for the rigid annuloplasty ring. After successful TMVR using a 29-mm Sapien 3 THV, the embolized valve was secured against the LA septum using a 35-mm Amplatzer septal occluder. Patient #5 suffered mild hemolysis, evident from low haptoglobin and elevated lactate dehydrogenase levels, and not requiring treatment. Post-procedure anemia resolved but haptoglobin remained depressed 4 months later. We suspect this is caused by mechanical red blood cell injury from flow across the THV struts, because there is no paravalvular leak.

TABLE 3

Complications and Clinical Outcomes

| Complications (n = 5) | |
|---|---|
| Valve embolization | 1 (20) |
| Paravalvular teak grade | None, n = 4 (80%) |
|  | Mild, n = 1 (20%) |
| Stroke | 0 |
| Bleeding major | 0 |
| Vascular major | 0 |
| Left ventricular perforation or pseudoaneurysm | 0 |
| Hemolysis | 1 (20) |
| Clinical outcomes (n = 5) | |
| Length of stay after TMVR, days | 8.6 ± 5.6 |
| Intensive care unit length of stay, days | 3.2 ± 2.7 |
| Survival to hospital discharge | 5 (100) |
| Survival 30 days | 4 (80) |
| Survival ascertainment, days | 132 (23-208) |

Values are n (%), n, mean ± SD, or median (range).
Abbreviation as in Table 1.

We have successfully lacerated the AML using a straightforward percutaneous technique (LAMPOON) immediately before TMVR in 5 patients. The technique resembles chordal-sparing AML resection that has become a standard in surgical mitral valve replacement (16,21). The technique succeeded in a range of different TMVR settings: mitral valve rigid ring annuloplasty, mitral valve semi-rigid ring annuloplasty mitral valve flexible posterior band annuloplasty, and native MAC. In patients deemed ineligible for TMVR because of predicted catastrophic LVOT obstruction or THV dysfunction, LAMPOON allowed TMVR without THV dysfunction and generated LVOT obstruction that was less than otherwise predicted.

The LAMPOON technique is important because 9% to 22% of patients selected to undergo TMVR in annuloplasty rings or native MAC experience critical LVOT obstruction. At present at least one-third of patients seem to be excluded from TMVR out of predicted risk of LVOT obstruction caused by the dis-placed AML. LAMPOON may allow TMVR in most, or perhaps all such excluded patients when using commercially available (uncovered) aortic THV devices off-label. Moreover, long or redundant native mitral leaflets have occasionally interfered with THV function either by direct mechanical interposition or by creating a low-pressure Bernoulli jet that impairs THV closure. Three of 5 patients had such long and redundant AMLs. The LAMPOON technique may pre-vent this THV dysfunction by displacing the split mitral leaflet. Finally, the LAMPOON strategy of split-ting the AML, combined with TMVR devices that allow flow across uncovered stent struts, should inform development of future dedicated TMVR devices.

Remarkably, no patient exhibited a change in heart rate or blood pressure in the short time interval be-tween LAMPOON mitral laceration and TMVR. In each case, echocardiography revealed acute exacerbation of mitral regurgitation. Acute mitral regurgitation caused by leaflet tethering is a recognized cause of hemodynamic deterioration in ante-grade trans-venous transseptal transcatheter aortic valve replacement, and unintentional guidewire laceration of the AML, in a tip-to-base fashion, is a recognized lethal complication of this approach. After LAMPOON, however, we observe a "grace period" that may reflect adaptation to left atrial volume and pressure overload from longstanding mitral stenosis or mitral regurgitation. Nonetheless, in every case we had pre-positioned the TMVR device in the left atrium to allow immediate implantation.

We did not observe severe mechanical complications of the LAMPOON procedure. One theoretical complication is injury to the aorta or aortic valve; we mitigated this risk by protecting the laceration wire surface using rigid braided guiding catheters. Another is mitral leaflet laceration through a lateral orifice of the mitral valve, which might leave a residual chorda that could prevent the split mitral leaflet from draping around the TMVR device. Another theoretical risk is of insufficiently basal traversal and laceration of the AML that causes insufficient leaflet debulking. We do not believe LAMPOON reduced stability of the THV implant; THV embolization in the first case reflected our mistaken selection of an undersized initial device. We attribute the observed low-grade hemolysis in patient #5 to nonlaminar flow across the THV struts as it spans across the LVOT. This would be classified as a mild complication according to the Mitral Valve Academic Research Criteria. Guidewire electrification may cause thromboembolism including cerebral thromboembolism; we mitigated this risk by anti-coagulation and by selecting ablative energies used in cardiac electrophysiology procedures.

There is compelling circumstantial evidence that LVOT obstruction would have been clinically important without LAMPOON, such as the finding that the THV straddled the full width of the LVOT cases #3 and #5. Based on available evidence, it may not be reasonable to offer TMVR without leaflet or septal debulking in patients with a low predicted neo-LVOT.

LAMPOON joins the family of transcatheter electrosurgery procedures. Originally limited to radiofrequency ablation of cardiac arrhythmias, transcatheter electrosurgery now includes atrial septal crossing by electrification of a Brockenbrough needle, and guidewire electrification for traversal of congenital cardiac lesions including pulmonic atresia and complete aortic coarctation, transcaval transcatheter aortic valve replacement, and coronary CTO traversal, among others.

By splitting the AML without surgery, LAMPOON allows successful TMVR in patients at risk of LVOT obstruction or THV dysfunction. Remarkably LAMPOON did not induce any short-term hemodynamic deterioration. Disrupting the native anterior leaflet, to allow blood flow across THV struts, can further improve TMVR devices and methods.

Transcatheter Laceration of Aortic Leaflets to Prevent Coronary Obstruction During Transcatheter Aortic Valve Replacement Transcatheter aortic valve replacement (TAVR) is an effective alternative to surgical aortic valve replacement in intermediate- and high-risk patients with native aortic stenosis. TAVR is also an effective treatment for failure of bioprosthetic surgical aortic valves, a treatment known as valve-in-valve TAVR. Coronary artery obstruction is a devastating complication of TAVR, with a greater than 50% mortality. Coronary artery obstruction occurs when the transcatheter heart valve displaces the underlying surgical or native aortic valve leaflets outwards and obstructs the coronary artery ostia, either by sealing the sinus of Valsalva at the sinotubular junction or by the leaflet itself covering the coronary ostia due to low lying coronary ostia and inadequate sinus width (see FIG. 7). Coronary artery obstruction is four times as common during valve-in-valve TAVR as during TAVR for native aortic stenosis, likely because most surgical prostheses are supra-annular in design, lowering coronary heights relative to the valve leaflets, and because valve suturing draws the coronaries closer, decreasing sinus width. The risk of coronary obstruction is highest during TAVR for surgical bioprothesis designs intended to maximize effective aortic orifice area (both "stented" bioprostheses that have externally mounted leaflets, and "stent-less" surgical bioprostheses). Treatment requires bail-out percutaneous coronary intervention, which may not be possible with a valve leaflet obstructing the coronary artery, or emergency bypass surgery. Pre-emptive coronary protection with a guidewire, with or without a coronary balloon or stent prepositioned down the coronary artery, is variably successful in the short and intermediate term. One third of coronary obstruction events may manifest after the TAVR is concluded.

We describe a solution based on the intentional Laceration of the Anterior Mitral leaflet to Prevent left ventricular Outflow Obstruction ("LAMPOON") procedure, which uses catheters to split the mitral valve leaflet and prevent obstruction of the left ventricular outflow tract during transcatheter mitral valve replacement. Here we report a technique to split aortic valve leaflets, whether bioprosthetic or native, to prevent coronary artery obstruction after TAVR. The new technique is called "BASILICA" (Bioprosthetic or native Aortic Scallop Intentional Laceration to prevent Coronary Artery obstruction).

We developed the technique in vitro and in animals, and then offered the procedure to patients suffering aortic valve failure who were ineligible for conventional surgical aortic valve replacement, and high or prohibitive risk of coronary artery obstruction from TAVR.

We demonstrate several key technical principles. First, that an aortic leaflet scallop can be traversed in situ by an electrified guidewire between the sinus of Valsalva and the left ventricular outflow tract. Second, that the traversed leaflet, whether native or bioprosthetic, can be lacerated in situ by the mid-shaft of an electrified guidewire. Third, that the lacerated leaflets splay after TAVR to allow blood flow across them towards otherwise obstructed coronary ostia. Fourth, whether partial (mid-scallop versus basal leaflet) lacerations extend lengthwise when stretched by an implanted valve, which may influence the required spatial precision of the procedure. Fifth, that both left and right coronary cusps can be lacerated simultaneously in vivo.

Figure 16:
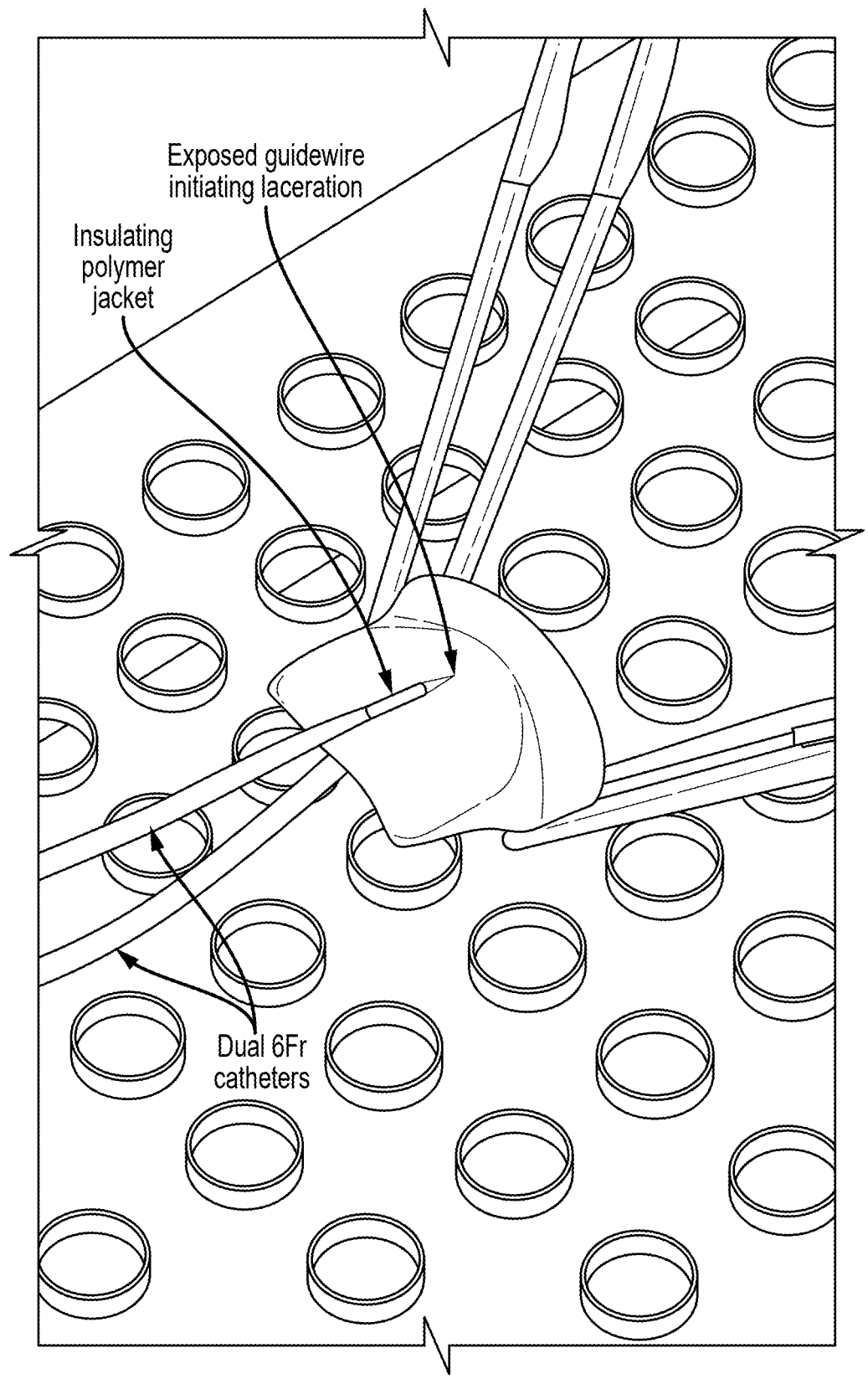
FIG. 16 shows a prosthetic heart valve with one leaflet being lacerated using the disclosed technology.

We tested radiofrequency-assisted transcatheter perforation and laceration of exterior mounted bovine pericardial leaflets on a representative bioprosthetic heart valve Trifecta valve, Abbott St Jude Medical) submerged in a 0.9% saline bath with a remote dispersive electrode (see FIG. 16). Two lacerations were attempted on the bioprosthetic heart valve. One leaflet was lacerated from base to tip and the second from midpoint to tip. A third scallop was left intact and served as a control.

Balloon expandable and self-expanding were deployed in the bioprosthetic valve to test splaying of split leaflet around the open cells of the transcatheter heart valve and propagation of the split in the leaflet. A second valve was cut with a scalpel and leaflet splaying was also tested with appropriately sized balloon expanding and self-expanding valves.

Animal experiments on naïve Yorkshire and Yucatan pigs were approved by the institutional animal care and use committee and conducted per contemporary NIH guidelines. Anesthesia was induced and maintained with mechanical ventilation and inhaled isoflurane, two 6 Fr femoral arterial sheaths and a 9 Fr femoral venous sheath were placed percutaneously, and heparin and amiodarone were administered. The BASILICA procedure without TAVR was performed using catheters directed under biplane X-ray fluoroscopy and intracardiac echocardiography guidance. Pre-procedural cardiac MRI was performed at 1.5 T. Hemodynamics were recorded for one hour after laceration till euthanasia. The length of scallop laceration relative to the overall length of the scallop was measured using calipers at necropsy. The heart was carefully inspected for evidence of bystander electrical or mechanical injury.

Patients with high or prohibitive risk for surgical aortic valve replacement and high risk of coronary artery obstruction with TAVR, underwent TAVR with BASILICA at three medical centers. All consented to clinical treatment on a compassionate basis, despite explicitly high risk, after consensus from the local multidisciplinary heart teams. The institutional ethics review boards of all participating institutions approved this retrospective report.

Figure 7A:
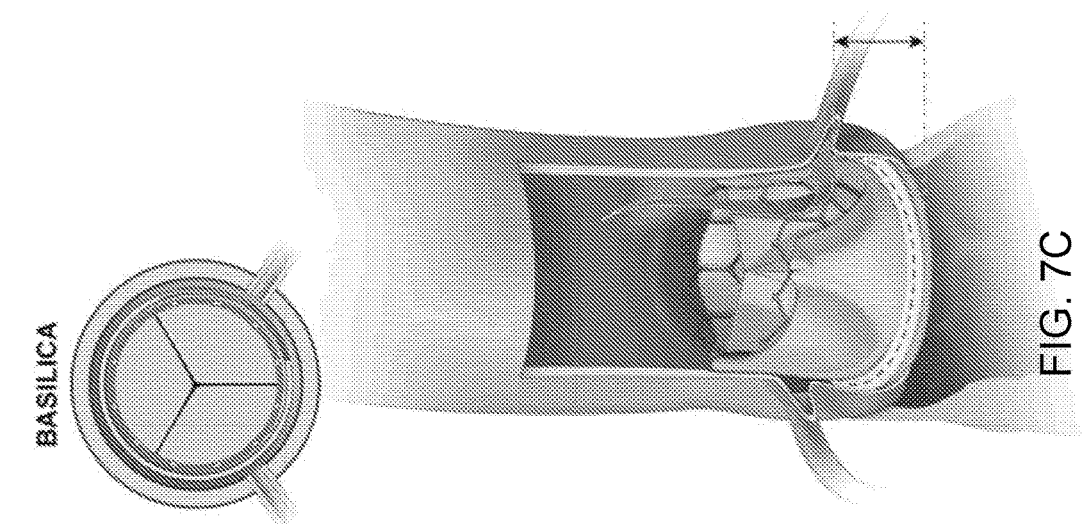
FIGS. 7A-7C illustrate coronary obstruction and prevention by Bioprosthetic or native Aortic Scallop Intentional Laceration to prevent Coronary Artery obstruction ("BASILICA").
Figure 7B:
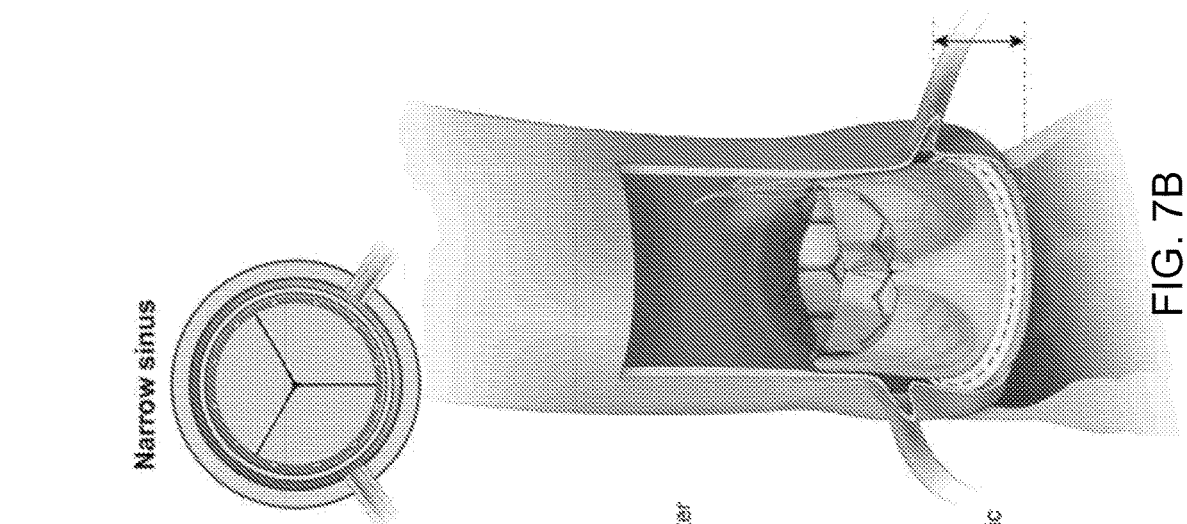
Figure 7C:
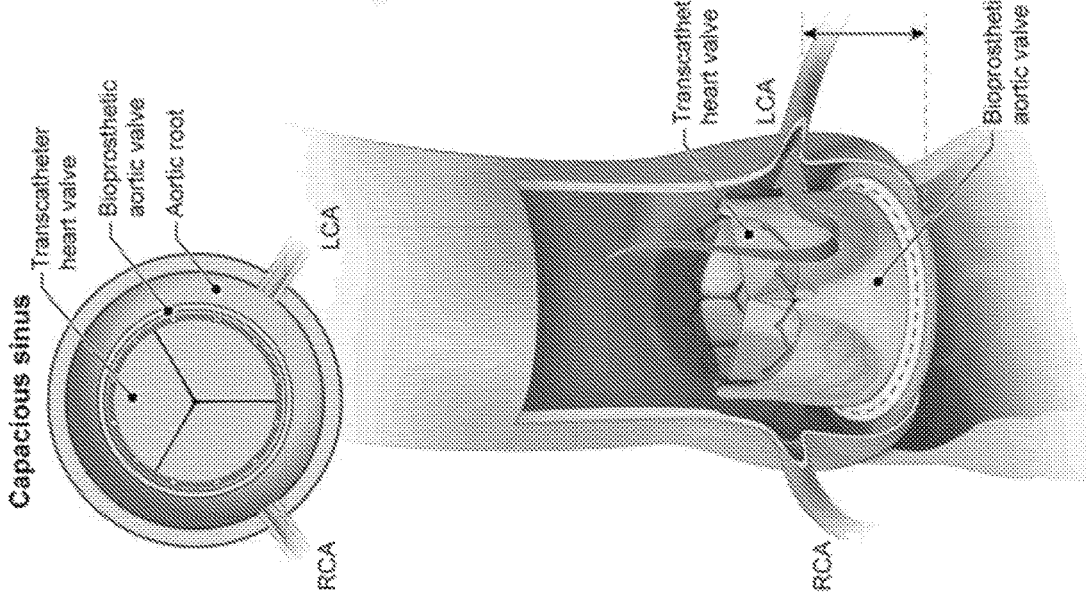
Figure 8A:
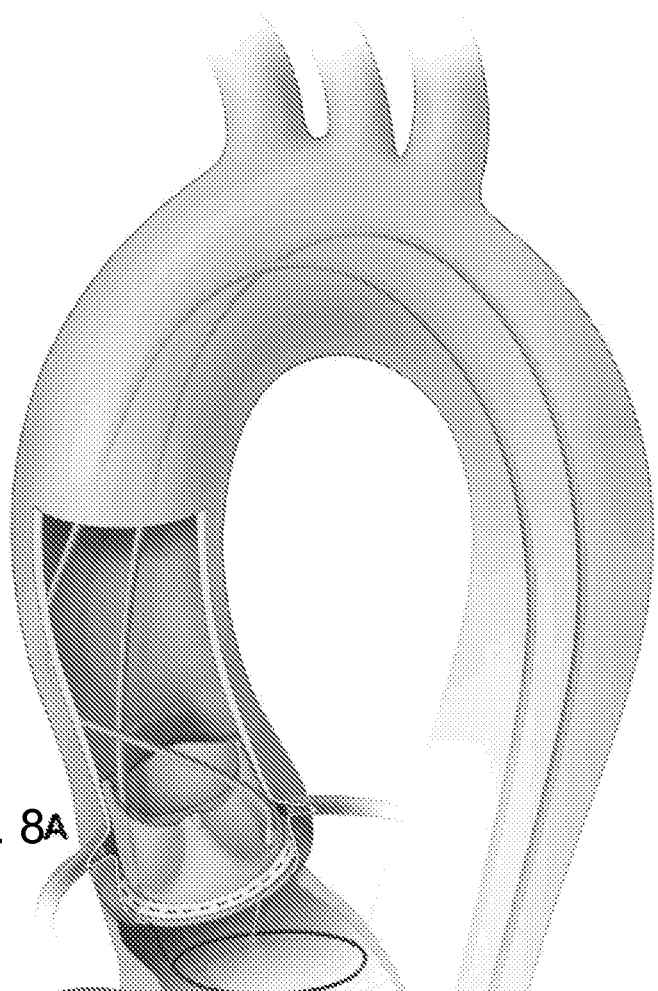
FIGS. 8A-8D illustrate the BASILICA procedure.
Figure 8B:
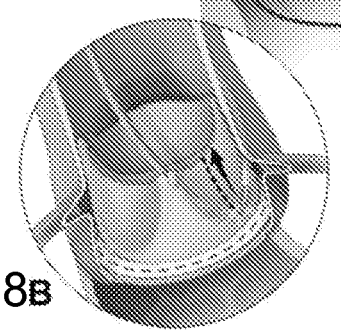
Figure 8C:
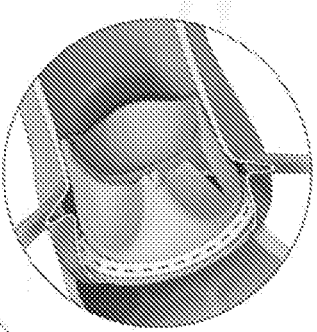
Figure 8D:
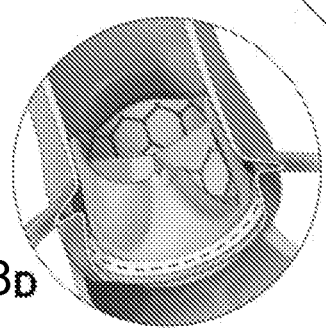

The local heart teams determined coronary obstruction risk based on manufacturer-described geometry of the specific implanted bioprosthetic valve; and CT and angiographic measurements of the coronary ostia heights, sinus of Valsalva width, presence and type of bioprosthetic valve, and virtual transcatheter heart valve to coronary (VTC) distance (FIG. 7).

The procedure was planned using ECG-gated contrast-enhanced CT, performed under general anesthesia, and guided by fluoroscopy and transesophageal echocardiography. Catheter access was obtained typically via three femoral arterial (two typically ipsilateral for BASILICA, and one for TAVR) and at least one venous (for temporary transvenous pacing) introducer sheaths. Heparin anticoagulation achieved an activated clotting time >300 s. A pair of coaxial catheters (typically a 5 Fr mammary diagnostic catheter inside a 6 Fr extra backup shape guiding catheter) was positioned in the targeted aortic leaflet scallop to direct a guidewire across it, near the scallop hinge point, by echocardiographic and angiographic guidance. These aimed at a snare positioned immediately below the leaflet using a separate retrograde catheter (FIG. 8).

To traverse the aortic leaflet scallop, an 0.014" guidewire sheathed in an insulated polymer jacket was electrified, advanced, and snare-retrieved. The wire was electrified using a short burst of "cutting" radiofrequency energy (~30 W) by clamping to an electrosurgery pencil.

After externalization of the free guidewire end, the guidewire straddles across the leaflet scallop between two catheters. The scallop was lacerated by applying radiofrequency energy at approximately 70 W while tensioning both free ends of the guidewire. A pigtail catheter was prepositioned in the left ventricle to allow TAVR to be performed immediately afterwards.

TAVR was performed using established techniques. Coronary artery stent systems were positioned prophylactically at the discretion of the operator. Cracking of a failed bioprosthetic heart valve frame, using a high-pressure balloon, was performed at operator discretion to achieve an optimum hemodynamic result. Coronary artery patency was assessed using angiography and post-TAVR CT. Antiplatelet and anticoagulation therapy were prescribed at operator discretion. Complications were assessed according to the Valve Academic Research Consortium-2 Consensus Document.

In this small clinical series, we express continuous variables that are not normally distributed as median and inter-quartile range, otherwise as mean±standard deviation. We express categorical variables as counts and percentages.

A guidewire (Astato XS 20, Asahi) perforated a bioprosthetic bovine pericardial valve leaflet using a <1 s burst of radiofrequency energy at 20 W in a saline bath. Laceration with a continuous non-ionic (5% dextrose) flush through two guiding catheters required 5 s (half leaflet) and 18 s (full leaflet) of radiofrequency energy at 20 W. Laceration using mechanical force without electrification was not possible in this valve.

A 20 mm Sapien 3 valve was deployed on the benchtop inside the lacerated Trifecta valve. The laceration mid-way down the bioprosthetic scallop did not propagate, nor did it result in satisfactory parting of the leaflet. The full-length laceration did not propagate further and resulted in satisfactory parting of the leaflet. The intact leaflet completely draped the S3 stent cells. The results with the cut Mitroflow valve were similar (FIG. 9). Flaring of the bioprosthetic stent posts increased splaying of the split leaflet.

Five consecutive pigs (38-47 kg) underwent attempted BASILICA, three on the left coronary cusp and two on both left and right coronary cusps (see Table 4). The procedure time reduced with further experience, despite the increased complexity of double BASILICA. BASILICA resulted in severe aortic regurgitation with a reduction in diastolic blood pressure in all pigs. Two pigs required euthanasia before one hour was complete due to poor hemodynamics—the first after inadvertent mitral chordal laceration, and the other following double BASILICA.

Figure 10:
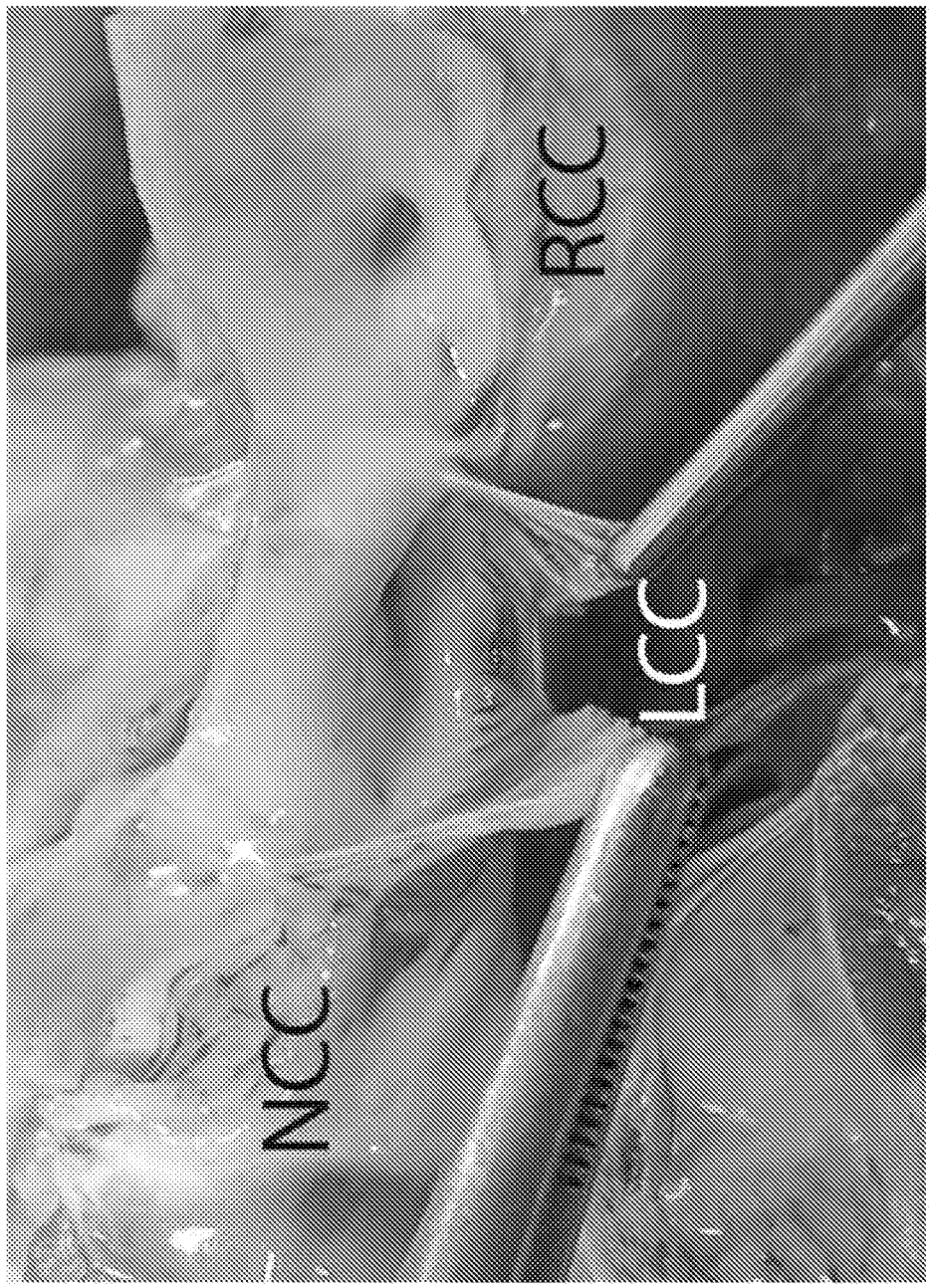
FIG. 10 illustrate animal necropsy viewed from the aorta showing a split left coronary cusp in line with the left coronary artery ostium. NCC=non-coronary cusp; LCC=left coronary cusp; RCC=right coronary cusp.
Figures 12A, 12B, 12C:
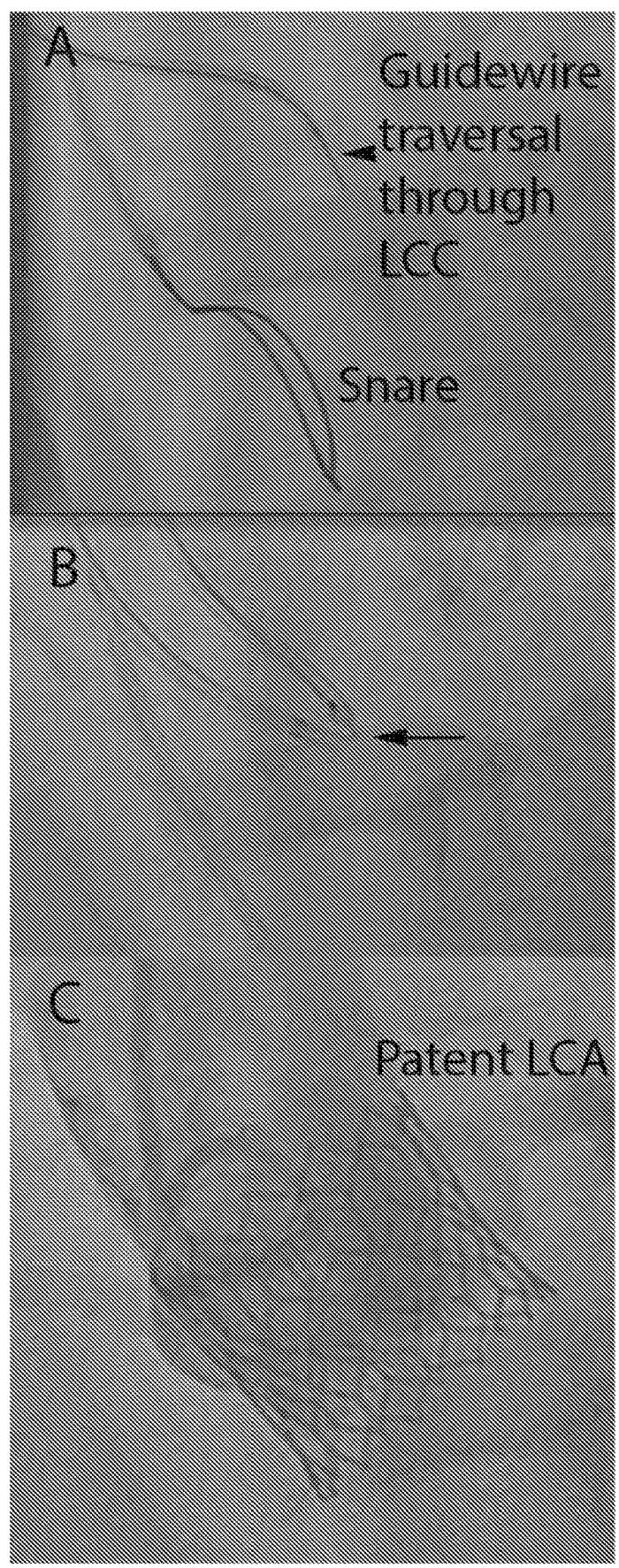
FIGS. 12A-12C illustrate BASILICA and TAVR with S3 for native aortic stenosis.
Figures 13A, 13B, 13C, 13D, 13E, 13F, 13G, 13H, 13I:
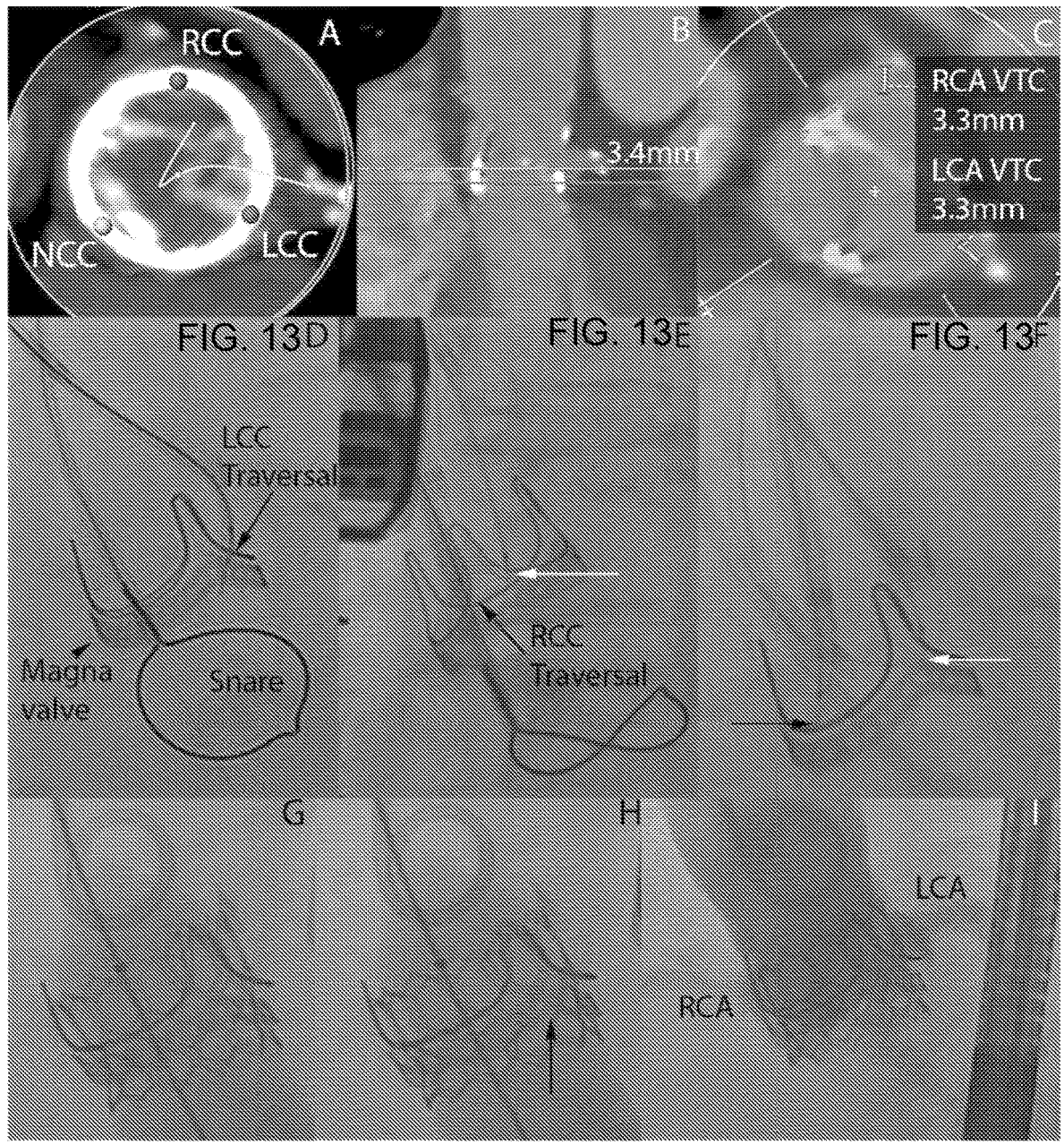
FIGS. 13A-13I illustrate double BASILICA and TAVR with S3 for failed *Magna* valve.

Guidewire traversal required <1 s of radiofrequency energy at 20-30 W for all five animals. Guidewire laceration required 2-3 s of radiofrequency energy at 30 W and <1 s at 70 W. Minimal subjective mechanical force was required for both traversal and laceration. Laceration was central and extended from base to tip in all animals (mean laceration length was 12 mm and mean cusp length 14 mm for the left, and 12 mm and 12.5 mm respectively for the right) (see FIG. 10).

Major complications occurred in the first attempted animal BASILICA for left and right coronary cusps respectively. These included mitral chord entrapment and laceration resulting in severe mitral regurgitation, misdirected wire traversal into the left atrium or interventricular septum, the latter causing ventricular fibrillation requiring defibrillation, and partial annular laceration without pericardial effusion from annulus rather than leaflet traversal. Thereafter we refined the BASILICA technique (assiduous positioning of the traversal wire and of the snare catheter in the distal left ventricular outflow tract) observed no important complications. There was no macroscopic evidence of collateral thermal damage in benchtop or in vivo necropsy specimens.

Seven patients underwent TAVR with BASILICA (FIGS. 11-15). There were a range of diseased aortic valve substrates: one had a porcine aortic stent-less bioprosthetic valve, one had a stentless bovine pericardial valve, four had stented bovine pericardial valves, and one had native aortic valve stenosis. One of the seven required laceration of two aortic leaflet scallops and the rest of only the left.

Table 4 shows their clinical characteristics. All were felt unsuitable for surgery by the multidisciplinary heart teams. Five had prior coronary artery bypass grafts that were felt not to protect threatened vessels. Six had failed bioprosthetic aortic valves and one had native aortic stenosis. All were felt to be at high risk of left coronary obstruction with median coronary height of 6.8 mm, left sinus of Valsalva width of 24.3 mm, and VTC of 2.8 mm. One patient also had a threatened right coronary artery (see Table 5).

TABLE 4

Clinical characteristics

| Patient number | ALL | 1 | 2 | 3 | 4 | 5 | 6 | 7 |
|---|---|---|---|---|---|---|---|---|
| Age | 74 (70-76) | 87 | 74 | 74 | 67 | 78 | 68 | 71 |
| Female sex | 86% | 1 | 1 | 1 | 0 | 1 | 1 | 1 |
| STS PROM aortic replacement % | 10.7% ± 1% | 13.40% | 4.6% | 19.5% | 2.0% | 12.7% | 8.0% | 14.7% |
| Frailty | 67% | 1 | 1 | 1 | 0 | 1 | 0 | NA |
| Coronary artery disease, binary | 71% | 1 | 1 | 0 | 1 | 0 | 1 | 1 |
| Prior CABG, % | 71% | 1 | 1 | 0 | 1 | 0 | 1 | 1 |
| Prior stroke, % | 14% | 0 | 0 | 0 | 0 | 0 | 0 | 1 |
| Atrial fibrillation, % | 57% | 1 | 0 | 1 | 0 | 1 | 0 | 1 |
| eGFR mL/min/1.73 m2 | 47.7 ± 19.4 | 60 | 31 | 12 | 62 | 51 | 65 | 53 |
| NT pro BNP baseline (pg/mL) | 738 ± 719 | 701 | 332 | 712 | 2145 | 262 | 275 | N.A. |
| NYHA CHF Class | 3.3 ± 0.5 | 4 | 3 | 4 | 3 | 3 | 3 | 3 |
| Severe pulmonary disease | 29% | 0 | 0 | 0 | 0 | 1 | 1 | 0 |
| LV ejection fraction | 53.3% ± 9.7% | 65% | 58% | 45% | 45% | 60% | 60% | 40% |
| RV dysfunction | 14% | 0 | 0 | 0 | 0 | 1 | 0 | 0 |
| Porcelain aorta | 14% | 0 | 0 | 0 | 0 | 0 | 1 | 0 |
| TAVR setting (native or valve-in-valve) | Valve-in-valve, 86% | Valve-in-valve | Valve-in-valve | Valve-in-valve | Valve-in-valve | Native | Valve-in-valve | Valve-in-valve |
| Bioprosthetic valve nominal diameter, mm | 21.3 ± 1.5 | 19 | 21 | 21 | 23 | NA | 21 | 23 |
| Bioprosthetic valve type | | Trifecta | Toronto SPV | Mitroflow | Mitroflow | NA | Magna | Sorin Solo Freedom SMT |
| Bioprosthetic implant age, years | 5 (3-11) | 6 | 14 | 4 | 3 | NA | 13 | 2 |
| Primary lesion | Regurgitation, 1; Stenosis, 2; Mixed, 2 | Regurgitation | Regurgitation | Mixed | Mixed | Stenosis | Stenosis | Regurgitation |
| Suitability for cardiac surgery | | Inoperable because of advanced age, marked frailty, and prospect of repeat cardiac surgery. | Inoperable because of grafts threatened by repeat surgery, marked frailty, and renal dysfunction | Inoperable because of class IV symptoms, prospect of combined mitral and aortic surgery after prior AVR, worsening kidney disease with | Prolonged recovery after prior MVR/AVR/CABG felt by surgical team better treated by catheter; Patient declined repeat surgery. | Inoperable because of very poor functional status and ongoing radiation therapy for thoracic malignancy | Prohibitively high operative risk with porcelain aorta, mitral annular calcification, prospect of ascending and root aorta repair along with | Inoperable because of NYHA Class IV symptoms, radiotherapy for malignancy, moderate left ventricular dysfunction, prior stroke, prior AVR + MVR + |

TABLE 4-continued

Clinical characteristics

| Patient number | ALL | 1 | 2 | 3 | 4 | 5 | 6 | 7 |
|---|---|---|---|---|---|---|---|---|
| | | | | creatinine >300 umol/L, recent cardiopulmonary arrest | | | AVR and MVR. | atrial ablation + LAA ligation. |

Figures 14A, 14B:
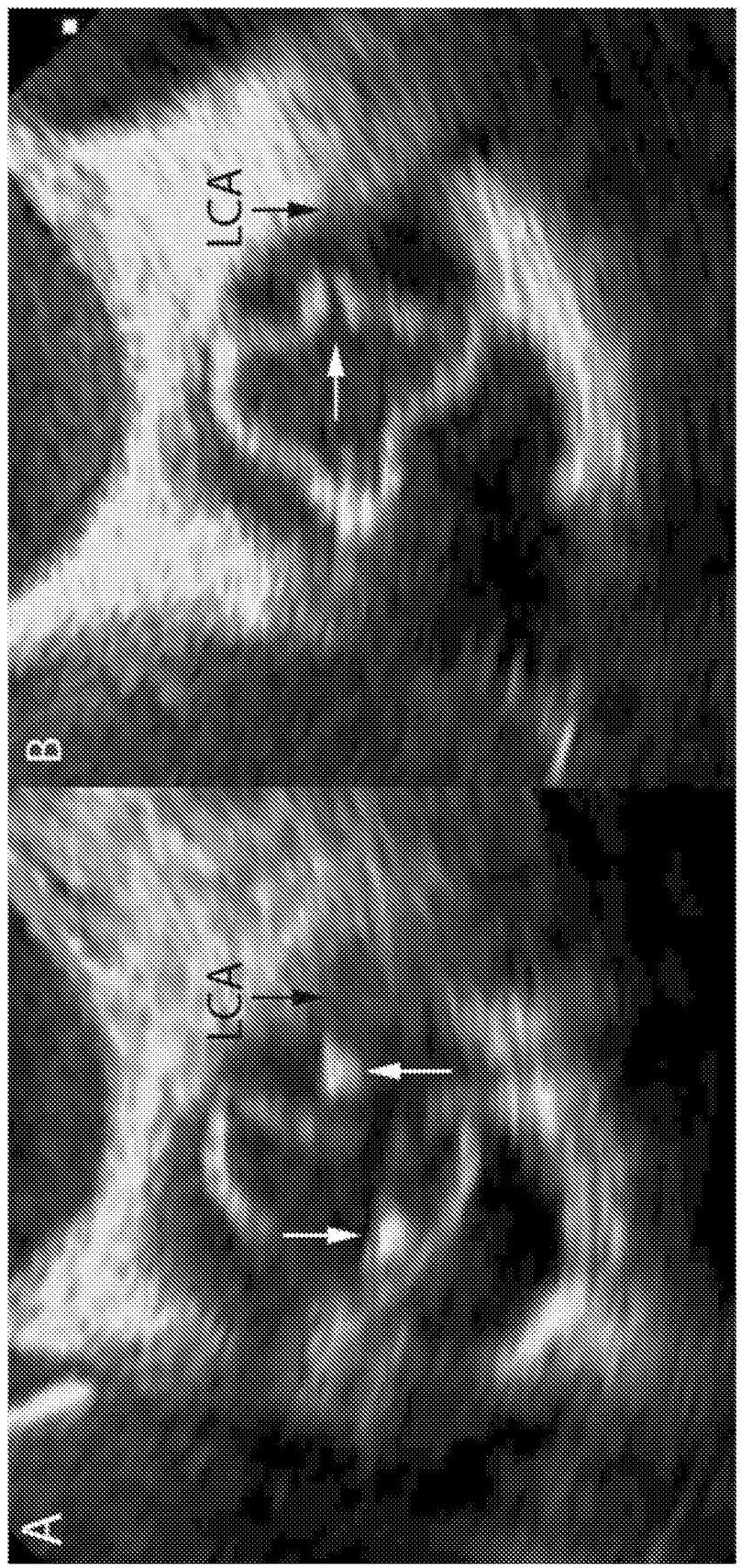
FIGS. 14A-14B illustrate transesophageal echocardiography during BASILICA and TAVR with S3 for failed Sorin Solo Freedom valve.

Table 5 below details the procedure. All attempted leaflets were successfully traversed and lacerated. The laceration was central and along most of the leaflet length as depicted on transesophageal echocardiography (FIG. 14B). All patients had severe aortic regurgitation after laceration. Heart rate and systolic blood pressures were unchanged in all cases, and no patient required pharmacologic or mechanical hemodynamic support in the 8-30 minutes between laceration and valve deployment, nor afterwards.

No patient had coronary obstruction evident on coronary and aortic root angiography, nor echocardiographic regional wall motion assessment. One of the pre-positioned stents was entrapped by the transcatheter heart valve and so was deployed in the left main coronary artery in the absence of coronary obstruction, otherwise all others were removed from the body undeployed. Procedural hemodynamics confirmed satisfactory valve gradients and no patient with more than mild paravalvular leak. Three patients had follow-up CT scans confirming good flow in the coronary arteries.

TABLE 5

Procedure characteristics and Hemodynamics

| Patient number | ALL | 1 | 2 | 3 | 4 | 5 | 6 | 7 |
|---|---|---|---|---|---|---|---|---|
| Transcatheter heart valve | Sapien 3, 6, Evolut Pro, 1 | Sapien 3 | Evolut Pro | Sapien 3 | Sapien 3 | Sapien 3 | Sapien 3 | Sapien 3 |
| Transcatheter heart valve size, mm | 22.6 ± 2.1 | 20 | 23 | 23 | 23 | 26 | 20 | 23 |
| Transcatheter heart valve post-dilation | 14% | 0 | 0 | 0 | 0 | 0 | 1 | 0 |
| Invasive Hemodynamics BASELINE | | | | | | | | |
| Aortic regurgitation severity (0 = None, 1 = Trace, 2 = Mild, 3 = Moderate, 4 = Severe) | 3.3 ± 1.0 | 4 | 4 | 4 | 3 | 2 | 2 | 4 |
| Aortic valve peak-to-peak gradient (mmHg) | 43 (14-64) | 12 | 8 | 43 | 72 | 56 | 135 | 15 |
| HR | 75 ± 7 | 84 | 72 | 67 | 77 | 69 | 83 | 75 |
| SBP | 125 ± 30 | 151 | 126 | 93 | 95 | 166 | 145 | 97 |
| DBP | 47 ± 14 | 32 | 47 | 35 | 53 | 73 | 42 | 44 |
| LVEDP | 28 ± 8 | 23 | 21 | 35 | 36 | 31 | 32 | 16 |
| Invasive Hemodynamics COMPLETION | | | | | | | | |
| Aortic regurgitation severity (0 = None, 1 = Trace, 2 = Mild, 3 = Moderate, 4 = Severe) | .6 ± .8 | 0 | 0 | 1 | 0 | 0 | 1 | 2 |
| Aoritc valve peak-to-peak gradient (mmHg) | 3.5 ± 5.0 | 1 | 10 | 1 | 12 | 0 | 0 | 3 |
| HR | 79 ± 9 | 80 | 82 | 85 | 79 | 62 | 87 | 40 (sinus brady - paced at 80) |
| SBP | 164 ± 26 | 177 | 151 | 175 | 120 | 181 | 197 | 150 |
| DBP | 68 ± 7 | 64 | 63 | 79 | 68 | 72 | 57 | 71 |
| LVEDP | 27 ± 5 | 34 | 28 | 26 | 26 | 27 | 18 | 31 |
| Echocardiography, Baseline | | | | | | | | |
| Aortic regurgitation severity (0 = None, 1 = Trace, 2 = Mild, 3 = Moderate, 4 = Severe) | 3.5 ± 8 | 4 | 4 | 3.5 | 4 | 3 | 2 | 4 |
| Aortic valve peak velocity (m/s) | 3.7 ± 1.3 | 3.3 | 3.1 | 5.6 | 4.1 | 3.4 | 5 | 1.6 |
| Aortic valve mean gradient (mmHg) | 33.8 ± 21.3 | 24 | 22 | 67 | 22.6 | 45.4 | 51 | 4.8 |
| Indexed effective orifice area (cm2/m2) | 0.8 ± 0.4 | 1 | 1.6 | 0.48 | 0.31 | 0.49 | 0.62 | 1.0 |
| LVEF | 52.6% ± 10.9% | 65% | 58% | 45% | 45% | 60% | 60% | 35% |
| Echocardiography, pre-discharge | | | | | | | | |
| Aortic regurgitation severity (0 = None, 1 = Trace, 2 = Mild, 3 = Moderate, 4 = Severe) | 0.1 ± 0.4 | 0 | 0 | 1 | 0 | 0 | 0 | 0 |

TABLE 5-continued

Procedure characteristics and Hemodynamics

| Patient number | ALL | 1 | 2 | 3 | 4 | 5 | 6 | 7 |
|---|---|---|---|---|---|---|---|---|
| Aortic valve peak velocity (m/s) | 1.8 ± 0.6 | 3.3 | 2.7 | 3.6 | 2.6 | 3.1 | 2.9 | 1.6 |
| Aortic valve mean gradient (mmHg) | 17.8 ± 7.0 | 17 | 16 | 28.2 | 17.6 | 21 | 20 | 4.8 |
| LVEF | 58.1% ± 11.9% | 71% | 64% | 61% | 51% | 60% | 65% | 35% |

Clinical outcomes and standardized TAVR endpoints are shown in TABLE 6 and Supplement Table 6. One patient had transient sinus bradycardia requiring temporary transvenous pacing. There were no other complications. Four patients underwent precautionary intensive care unit observation overnight; the remainder were transferred directly to ward beds. The median length of stay was 4 days. All patients survived beyond 30 days.

TABLE 6

Clinical outcomes

| Patient number | ALL | 1 | 2 | 3 | 4 | 5 | 6 | 7 |
|---|---|---|---|---|---|---|---|---|
| Length of stay after TAVR (days) | 4 (4-5) | 4 | 4 | 6 | 1 | 5 | 5 | 3 |
| ICU stay (days) | 1 (0-2) | 2 | 2 | 0 | 0 | 1 | 1 | 0 |
| Survival to hospital discharge | 100% | 1 | 1 | 1 | 1 | 1 | 1 | 1 |
| Survival 30 d | 100% | 1 | 1 | 1 | 1 | 1 | 1 | 1 |
| Survival ascertainment days | 39 (15-77) | 77 | 77 | 74 | 39 | 32 | 32 | 18 |
| NYHA Class at latest follow-up | 1.7 ± 0.5 | 2 | 2 | 1 | 2 | 1 | 2 | 2 |

We describe a new technique that allows transcatheter heart valve treatment in patients otherwise ineligible for any therapy because of a high risk of valve leaflet-induced coronary artery obstruction. We have demonstrated through benchtop testing, animal experiments, and experience from seven patients that BASILICA appears technically feasible in all valve types and valve conditions, including single and double leaflet laceration, porcine and bovine pericardial bioprostheses, stented and stent-less bioprostheses, and in one case of native aortic leaflet disease, there was no hemodynamic collapse after laceration regardless of baseline aortic regurgitation or aortic stenosis, an there was uniform success in preserving coronary blood flow.

The current strategy of ad-hoc percutaneous intervention or up-front coronary protection using a pre-positioned wire, with or without balloon or stent, is problematic. Coronary obstruction may be delayed despite normal flow at the end of the TAVR procedure. There are few data to support the longevity of a "chimney" coronary stent extending beyond the coronary ostium with a valve leaflet draped across it. The ostial left main stent is at risk of fatal restenosis and thrombosis. Re-engaging a coronary artery is challenging after TAVR, and becomes almost impossible with an ostial "chimney" stent. As seen in one patient #7, the stent can be entrapped and then requires unnecessary deployment. Applying caution in this initial human experience, the threatened coronaries were still protected by wiring and placing a stent midvessel after BASILICA. While the one entrapped stent confirmed the preprocedural concern for coronary obstruction and need for intervention to allow safe TAVR, the inability to remove the stent necessitated deployment despite otherwise successful BASILICA. It is difficult to know at this early stage whether pre-positioning a stent after successful BASILICA is mandated or whether the harm outweighs the benefits. As experience with BASILICA and its success increases, we would predict a transition to no prophylactic coronary stent protection.

One application of BASILICA not yet performed but worth considering is to treat failed TAVR devices, which are likely to become more common as TAVR is applied to lower risk patients who are expected to live longer. The risk of coronary obstruction in patients with previous TAVR may be elevated in patients with high implantation and supra-annular TAVR devices engineered to have longer leaflets (such as Medtronic CoreValve). Several transcatheter heart valves are implanted with the top of the valve at the sinotubular junction where coronary filling is dependent on diastolic valve-leaflet closure. We speculate that BASILICA may be helpful in this setting. In this small series, we observed that split leaflets continued to appose during diastole, and caused incremental but not catastrophic aortic regurgitation. Patients did not require pharmacologic or mechanical support during the short period before TAVR.

We observed no hemodynamic deterioration between BASILICA laceration and TAVR in this small series. Our patients had relatively preserved left ventricular systolic function (Table 4). Two of seven had primarily stenotic lesions and three of seven primarily mixed stenotic and regurgitant. BASILICA can be combined with intentional balloon fracture to expand the valve frame. Double leaflet BASILICA can also be performed. Heavily calcified leaflets may or may not be suitable for BASILICA.

There were no evident strokes in this initial series. Because lacerating a heavily calcified leaflet may generate embolic debris that could possibly cause stroke in this setting, judicious use of cerebral embolic protection strategies and brain MRI can also be included in the procedures. Compared to protracted radiofrequency ablation employed in the left atrium and left ventricle, we use shorter bursts of vaporizing high duty-cycle "cutting mode" electrosurgery, also with full anticoagulation.

In summary, bioprosthetic and native aortic leaflet laceration appears feasible and may reduce the risk of coronary artery obstruction following TAVR in patients at high risk. No patient had a drop in blood pressure following BASILICA. The technique offers a promising alternative to "chimney" stenting to provide durable prevention against coronary obstruction from TAVR.

Inner Curvature Charge Concentration for Tissue Laceration

The following are exemplary problems that can be solved by the herein disclosed technology. This list is not exclusive, this technology can provide additional advantages, and not every problem-solution listed is necessarily applicable to each embodiment of the disclosed technology.

1. The problem of cutting tissue such as a heart valve can be solved by electrifying a traversing metallic conductor (lacerator) while applying traversal force.
2. The problem of charge dispersion from an electrified (monopolar) traversing metallic conductor (above) can be solved by insulating the lacerator except where it traverses the target tissue.
3. The problem of longitudinally aligning the lacerator with the target tissue can be solved by intentionally kinking the guidewire.
4. The problem of charge concentration on the outer curvature of an intentionally kinked traversing metallic conductor can be solved by focally insulating the outer curvature, or conversely, by focally denuding the lacerator insulation at the inner curvature where contact is made with target tissue.
5. In parallel the problem of an electrified kinked and focally denuded lacerator requiring an indifferent electrode can be solved by creating a kinked bipolar electrode, separated by insulation.
6. The problem of electrode carbonization, local thrombus formation, and tissue escharification can be solved by irrigating the target tissue during lacerator electrification using a non-conductive non-ionic biocompatible liquid, such as isotonic (5%) dextrose or non-ionic radiocontrast. The solution can be embodied by combining the lacerator with an irrigator.

In one exemplary procedure, intentional Laceration of the Anterior Mitral leaflet to prevent left ventricular Outflow Obstruction (LAMPOON), the mitral leaflet is lacerated to allow implantation of a transcatheter heart valve in order to keep the leaflet from getting pushed anterior towards the interventricular septum. The procedure has been successfully applied in at least 30 patients to date.

In another exemplary procedure, Bioprosthetic Aortic Scallop Intentional Laceration to prevent Iatrogenic Coronary Artery obstruction during transcatheter aortic valve replacement (BASILICA), the aortic leaflet is lacerated to prevent occlusion of a coronary artery from the new valve pushing the old valve leaflet outwards. The problem is more common for "valve-in-valve" TAVR, but is an important problem for about 1-2% of TAVR, a significant number of patients. The procedure has been applied in at least 13 patients to date. BASILICA will have increased value as new TAVR devices age and increasingly fail, and require TAVR-in-TAVR.

A third procedure, Electrosurgical Laceration of Alfieri STItCh (ELASTIC), has been performed in at least one patient. It has application in treating Mitra-Clip failure, for example. The applicability is likely to be thousands or tens-of-thousands per year.

FIG. 17 illustrates a basic example of using an energized wire (in blue), or "lacerator," to lacerate a valve leaflet via a percutaneous process. The energized wire can vaporize the tissue in contacts, using heat generated as electricity flows through the wire and tissue. In any of the disclosed lacerator embodiments, the wire can be used to deliver any amount of energy, such as from about 50 W to about 100 W. In some embodiments, the electricity can flow in one direction, in alternating current, high frequencies such radio frequency, and/or other manners. A dispersal electrode can be position nearby to complete the electrical circuit, forming a "monopolar" modality. In addition, the area around the lacerator can be filled/irrigated with a non-ionic biocompatible liquid, such as 5% dextrose, distilled water, non-ionic radio-contrast, etc., to displace blood from around the lacerator and help reduce the formation of char and coagulum.

FIG. 18 illustrates an exemplary monopolar lacerator that is electrically insulated except for a local exposed or denuded region (yellow). In any of the disclosed embodiments, the exposed region(s) can extend less than 180 degrees, less than 90 degrees, and/or less than 60 degrees, around the circumference of the wire. In any of the disclosed embodiments, the exposed region(s) can extend longitudinally less than 10 mm, less than 5 mm, less than 4 mm, and/or approximately 3 mm. This can concentrate the current and generated heat to focus on a particular portion of tissue that is contacted by the exposed region, preventing remote current and heat dispersion, and avoiding unintentional tissue damage. In any of the disclosed examples, the insulation can comprise a polymeric coating, such as PTFE or the like. In addition, the area around the lacerator can be filled/irrigated with a non-ionic biocompatible liquid, such as 5% dextrose, distilled water, non-ionic radio-contrast, etc., to displace blood and further insulate the lacerator and help reduce the formation of char and coagulum.

FIG. 19 illustrates another exemplary monopolar lacerator that is insulated except for a local exposed region (yellow). In addition, the lacerator can be kinked or curved at the exposed location, as shown, with the exposed region being located on the inside of the kink/curve. As used herein, the term "kink" means any locally defined bend or curve in the wire. In any of the kinked or curved embodiments, the kink or curve can have an internal angle of less than 180 degrees, such as less than 150 degrees, less than 120 degrees, less than 90 degrees, less than 60 degrees, and/or less than 30 degrees. This can cause the exposed region to saddle over the leaflet edge, and help align the exposed region of the lacerator with the intended tissue to be lacerated. This can also concentrate the current and heat to focus on a particular portion of tissue that is contacted by the exposed region, preventing remote current and heat dispersion, and avoiding unintentional tissue damage. In addition, the area around the lacerator can be filled/irrigated with a non-ionic biocompatible liquid, such as 5% dextrose, distilled water, non-ionic radio-contrast, etc., to displace blood and further insulate the lacerator and help reduce the formation of char and coagulum.

FIG. 20 illustrates yet another exemplary lacerator 100 that is insulated except for two (or more) exposed regions 102a, 102b. In addition, the lacerator can be bent/kinked or curved adjacent the exposed regions 102a, 102b, as shown, with the exposed regions being located opposing each other on the inner side of the bend/curve 104. This can cause the exposed regions 102a, 102b to saddle over/around the leaflet edge, and help align the exposed regions of the lacerator with the intended tissue to be lacerated. In this embodiment, the two exposed regions 102a, 102b can have opposite polarity, forming a "bipolar" lacerator, such that electrical current flows from one exposed region to the other exposed region through the tissue. This can concentrate the current flow and generated heat on a particular portion of tissue 106 that between the two exposed regions 102a, 102b in the bend/curve of the lacerator 100. This can also help prevent remote current and heat dispersion, and avoid unintentional tissue damage. In addition, the area around the lacerator 100 can be filled/irrigated with a non-ionic biocompatible liquid, such as 5% dextrose, distilled water, non-ionic radio-contrast, etc., to displace blood and further insulate the lacerator and help reduce the formation of char and coagulum.

The lacerators described with reference to FIGS. 17-20, and related lacerating and irrigation methods, can be used in any of the methods disclosed herein.

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Features, integers, characteristics, or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods.

As used herein, the terms "a", "an", and "at least one" encompass one or more of the specified element. That is, if two of a particular element are present, one of these elements is also present and thus "an" element is present. The terms "a plurality of" and "plural" mean two or more of the specified element. As used herein, the term "and/or" used between the last two of a list of elements means any one or more of the listed elements. For example, the phrase "A, B, and/or C" means "A", "B,", "C", "A and B", "A and C", "B and C", or "A, B, and C." As used herein, the term "coupled" generally means physically, chemically, electrically, magnetically, or otherwise coupled or linked and does not exclude the presence of intermediate elements between the coupled items absent specific contrary language.

In view of the many possible embodiments to which the principles of the disclosed technology may be applied, it should be recognized that the illustrated embodiments are only examples and should not be taken as limiting the scope of the disclosure. Rather, the scope of the disclosure is at least as broad as the following claims. We therefore claim all that comes within the scope of these claims.

The invention claimed is:

1. A focally denuded electrosurgical lacerator for use in a fluid filled region of a patient, the lacerator comprising: a wire having a proximal end and a distal end, wherein the proximal end is spaced apart from the distal end; and wherein the wire is at least partially covered by electrical insulation and comprises a V-shaped kink having an acute angle, wherein the wire is exposed through the insulation at two continuous, exposed and non-circumferentially focally denuded regions on an inner curvature of the V-shaped kink, the continuous, exposed and non-circumferentially focally denuded regions extending less than 180 degrees around a circumference of the wire and collectively forming a cutting edge, wherein the two continuous, exposed and non-circumferentially focally denuded regions are provided proximal to and on opposing sides of the V-shaped kink, wherein the continuous, exposed and non-circumferentially focally denuded regions form a saddle operable to align the denuded regions with a tissue target, and a remainder of an inner surface of the wire is insulated, and wherein an entire length of an outer circumference of the lacerator is insulated and devoid of exposed regions to limit remote current and heat dispersion, the outer portion comprising an outer portion of the lacerator relative to the inner curvature and the cutting edge;

a radiopaque marker provided adjacent the cutting edge;

wherein at least one of the proximal end and the distal end of the wire is configured to be connected to an electrosurgical generator and the wire is configured to conduct electrical energy through and between the two continuous, exposed and non-circumferentially focally denuded regions and through the tissue target positioned between the two exposed regions in the inner curvature to lacerate the tissue target via the electrical energy.

2. The lacerator of claim 1, wherein the electrical energy is operable to lacerate the tissue target that comprises a native heart valve leaflet or a prosthetic heart valve leaflet.

3. The lacerator of claim 1, wherein the V-shaped kink defines an internal angle that is less than 30 degrees.

4. The lacerator of claim 1, wherein the two exposed regions are positioned facing each other.

5. The lacerator of claim 1, wherein the two exposed regions are positioned on opposite ends of the V-shaped kink.

6. The lacerator of claim 1, wherein the two exposed regions each extend less than 5 mm longitudinally.

7. The lacerator of claim 1, wherein the lacerator is operable to conduct from 50 W to 100 W of energy between the two exposed regions through the tissue target.

8. The lacerator of claim 1, wherein the lacerator is configured to be delivered percutaneously or transvascularly into a patient's heart.

9. The lacerator of claim 1, further comprising an irrigation catheter configured to introduce a non-ionic liquid adjacent to the two exposed regions to displace blood from around the two exposed regions.

10. A method comprising lacerating a native or prosthetic heart valve leaflet within a patient's heart using the lacerator of claim 1.

11. The method of claim 10, wherein the method comprises LAMPOON, BASILICA, or ELASTIC.

12. An electrosurgical lacerator for use in a fluid filled space within a patient, the lacerator comprising: a wire having a proximal end and a distal, wherein the proximal end is spaced apart from the distal end, and the wire is at least partially covered by electrical insulation, wherein the wire has a V-shaped kink defining an acute angle of less than 90 degrees, wherein the wire comprises an inner region having a cutting edge and an outer region;

the inner region comprising an inner half of a circumference of the wire on an inner curvature of the V-shaped kink;

the outer portion comprising an outer half of a circumference of the wire on an exterior portion of the V-shaped kink and provided on an opposing side of the lacerator relative to the cutting edge;

wherein the wire is exposed through the insulation along a continuous and focally denuded region solely on the inner curvature forming a cutting edge, wherein the continuous and focally denuded region is provided such that the wire is exposed on both inner sides of the V-shaped kink and wherein an entire length of the outer portion of the lacerator is insulated and devoid of exposed regions to limit remote current and heat dispersion, and wherein the continuous and focally denuded region forms a saddle operable to align the denuded region with a tissue target and a remainder of an inner surface of the wire is insulated;

wherein at least one of the proximal end and the distal end of the wire is connected to an electrosurgical generator; and wherein the wire is configured to conduct electrical energy through the continuous and focally denuded region and through a tissue target positioned in the inner curvature to lacerate the tissue target via the electrical energy.

* * * * *